(12) United States Patent
Niewöhner et al.

(10) Patent No.: US 6,803,365 B2
(45) Date of Patent: Oct. 12, 2004

(54) IMIDAZO[1,3,5]TRIAZINONES AND THE USE THEREOF

(75) Inventors: Ulrich Niewöhner, Wermelskirchen (DE); Helmut Haning, Milford, CT (US); Thomas Lampe, Wuppertal (DE); Mazen Es-Sayed, Langenfeld (DE); Gunter Schmidt, Wuppertal (DE); Erwin Bischoff, Wuppertal (DE); Klaus Dembowsky, Boston, MA (US); Elisabeth Perzborn, Wuppertal (DE); Karl-Heinz Schlemmer, Wuppertal (DE)

(73) Assignee: Bayer Aktlengesellschaft, Leverkusen (DE)

(*) Notice: Subject to any disclaimer, the term of this patent is extended or adjusted under 35 U.S.C. 154(b) by 0 days.

(21) Appl. No.: 10/168,194

(22) PCT Filed: Dec. 12, 2000

(86) PCT No.: PCT/EP00/12597

§ 371 (c)(1),
(2), (4) Date: Nov. 4, 2002

(87) PCT Pub. No.: WO01/47928

PCT Pub. Date: Jul. 5, 2001

(65) Prior Publication Data

US 2003/0195210 A1 Oct. 16, 2003

(30) Foreign Application Priority Data

Dec. 24, 1999 (DE) .......................................... 199 62 928
Jan. 27, 2000 (DE) .......................................... 100 03 323

(51) Int. Cl.$^7$ ............................................. C07D 487/04
(52) U.S. Cl. ............... 514/246; 514/212.08; 514/236.2; 540/524; 544/112
(58) Field of Search ............................... 544/220, 112; 514/246, 212.08, 236.2; 540/524

(56) References Cited

U.S. PATENT DOCUMENTS 5,482,941 A   1/1996   Terrett .......................... 514/253
5,591,742 A   1/1997   Bell et al. .................. 514/234.5
6,362,178 B1  3/2002   Niewohner et al. ......... 514/218

FOREIGN PATENT DOCUMENTS

EP   0463756   1/1992
EP   0951908   10/1999
WO   9428902   12/1994
WO   9719947   6/1997
WO   9849166   11/1998

OTHER PUBLICATIONS

Golankiewicz, B., Januszczyk, P., Ikeda, S., Balzarini, J., and De Clercq, E., "Synthesis and Antiviral Activity of Benzyl–Substituted Imidazo[1,5–a]–1,3,5–triazine(5, 8–Diaza–7.9–dideazapurine) Derivatives", J. Med. Chem., 38: 3558–3565 (1995).

Golankiewicz, B., Januszczyk, P., Zeidler, J., Popenda, M., Bartoszak, E., and Kosturkiewicz, Z., "The Route from 4–Oxo– to 4–Amino–imidazo[1,5–a]–1,3,5–triazines and the Tautomerism of 4–Oxo, 4–Thioxo and 4–Oxo–2–thioxo Derivatives. A $^1$H and $^{13}$C NMR and X–Ray Crystollographic Study", J. Chem. Res.(S): 96–97 (1994).

Golankiewicz, B., Holtwick, J. B., Holmes, B. N., Duesler, E. N., Leonard, N. J., "Synthesis of Imidazo[1,5–a]–1,3, 5–triazinones by Cyclization–Rearrangement", J. Org. Chem., 44(10): 1740–1742 (1979).

Golankiewicz, B., Zeidler, J., and De Clercq, E., "Synthesis and Biological Activity of C–Acyclic Nucleosides of Imidazo [1,5–a]–1,3,5–Triazines", Nucleosides & Nucleotides, 6(4): 663–678 (1987).

Holtwick, J. B., Golankiewicz, B., Holmes, B. N., and Leonard, N. J., "Guanine, Hypoxanthine, and Xanthine Analogues. Synthesis of Imidazo[1,5–a]–1,3,5–triazinones via Rearrangement", J. Org., Chem., 44(22): 3835–3839 (1979).

Holtwick, J. B., and Leonard, N. J., "Guanine Analogues. Allyl–Substituted Aminoimidazo[1,5–a]–1,3,5–triazinones Formed by Cyclization–Rearrangement", J. Org. Chem., 46: 3681–3685 (1981).

Wang, Y., Wheelhouse, R. T., Zhao, L., Langnel, D. A. F., and Stevens, M. F. G., "Antitumor Imidazotetrazines. Part 36. Conversion of 5–amino–imidazole–4–carboxamide to imidazo[5,1–d][1,2,3,5]tetrazin–4(3H)–ones and imidazo[1, 5–a][1,3,5]triazin–4(3H)–ones related in structure to the antitumour agents temozolmide and mitozolomide", J. Chem. Soc., Perkin Trans. 1. pp. 1669–1675 (1998).

Wang, Y., and Stevens, M. F. G., "Synthetic Studies of 8–Carbamoylimidazo–[5,1–D]–1,2,3, 5–Tetrazin–4(3H)–one: A Key Derivative of Antitumor Drug Temozolmide", Bioorganic & Medicinal Chemistry Letters, 6(2): 185–188 (1996).

Beavo, J., Reifsnyder, D., "Primary Sequence of Cyclic Nucleotide Phosphodiesterase Isozymes and the Design of Selective Inhibitors", TIPS Reviews, 11: 150–155 (1990).

Rao, T., Revankar, G., "Synthesis of Certain Acyclic Nucleoside Analogs of 1,2,4–Triazolo[3,4–*f*][1,2,4]Triazine and Pyrimido[5,4–*d*]Pyrimidine", Nucleosides & Nucleotides, 14(7): 1601–1612 (1995).

(List continued on next page.)

*Primary Examiner*—Richard L. Raymond
(74) *Attorney, Agent, or Firm*—Susan M. Pellegrino

(57) ABSTRACT

The invention relates to imidazo[1.3.5]triazinones, a method for their production and methods of use, in particular as inhibitors of cyclic GMP metabolizing phosphodiesterases.

9 Claims, No Drawings

OTHER PUBLICATIONS

Bhattacharya, B., Rao, T., Lewis, A., Revankar, G., "Synthesis of Certain N– and C–Alkyl Purine Analogs", J. Heterocyclic Chem., 30: 1341–1349(1993).

Mitchell, W., Hill, M., Newton, R., Ravenscroft, P., Scopes, D., "Synthesis of C–Nucleoside Isosteres of 9–(2–Hydroxyethoxymethyl) Guanine (Acyclovir) [1]", J. Heterocyclic Chem., 21: 697–699(1984).

Stoclet, J., Keravis, T., Komas, N., Lugnier, C., "Cyclic Nucleotide Phosphodiesterases as Therapeutic Targets in Cardiovascular Diseases", Exp. Opin. Invest. Drugs, 4(11): 1081–1100 (1995).

Kobe, B., Kobe, J., Smee, D., Dzonova, B., Solmajer, T., "Use of Distance Geometry Approach for the In Vitro Antiviral Activity Evaluation of N–Bridgehead C–Nucleosides", Eur. J. Med. Chem., 27: 259–266 (1992).

Correction: Chem. Abstr. XP–000926539, Golankiewicz, B., Januszczyk, P., Ikeda, S., Balzarini, J., Clercq, E., "Synthesis and Antiviral Activity of Benzyl –Substituted Imidazo [1,5–a]–1,3,5–triazine (5,8–Diaza–7,9–Dideazapurine) Derivatives", J. Med. Chem., 39: 624 (1996).

IMIDAZO[1,3,5]TRIAZINONES AND THE USE THEREOF

This is a 371 application of PCT/EP00/12597, filed Dec. 12. 2000.

The present invention relates to novel imidazo[1,3,5] triazinones, to processes for preparing them and to their use as medicaments, in particular as inhibitors of cGMP-metabolizing phosphodiesterases.

The synthesis of imidazo[1,3,5]triazinones is described in J. Org. Chem. (1979), 44(10), 1740–2; in J. Org. Chem. (1979), 44(22), 3835–9; in J. Org. Chem. (1981), 46 (18), 3681–5 and J. Chem. Res. Synop. (1994), (3), 96–7. These publications did not report any biological effect.

Imidazo[1,3,5]triazinones which possess antiviral and/or antitumor effect are described in Nucleosides Nucleotides (1987), 6(4), 663–78; in Eur. J. Med. Chem. (1992), 27(3), 259–66; in J. Heterocycl. Chem. (1993), 30(5), 1341–9; in J. Med. Chem. (1995), 38(18), 3558–68 and Biorg. Med. Chem. Lett. (1996), 6(2), 185–8. The compounds which are mentioned in these literature references were for the most part prepared as guanine or guanosine analogs and are therefore as a rule substituted in the 2 position by —NH$_2$, —SH or —H. None of the compounds which are described contains a phenyl ring or a substituted phenyl ring in the 2 position. None of the compounds which are described has been reported to have an inhibitory effect on phosphodiesterases.

The compounds according to the invention are potent inhibitors of cyclic guanosine 3',5'-monophophate-metabolizing phosphodiesterases (cGMP-PDEs). In accordance with the nomenclature of Beavo and Reifsnyder (Trends in Pharmacol. Sci. 11, 150–155, 1990), these phosphodiesterases are the phosphodiesterase isoenzymes PDE-I, PDE-II and PDE-V.

An increase in the concentration of cGMP can lead to therapeutic, antiaggregatory, antithrombotic, antiproliferative, antivasospastic, vasodilatory, natriuretic and diuretic effects. It can exert an effect on the short-term or long-term modulation of vascular and cardiac inotropy, cardiac rhythm and stimulus conduction in the heart (J. C. Stoclet, T. Keravis, N. Komas and C. Kugnier, Exp. Opin. Invest. Drugs (1995), 4 (11), 1081–1100). Inhibition of the cGMP-PDEs can also strengthen erection. These compounds are therefore suitable for treating erectile dysfunction.

The present invention now relates to novel imidazo[1,3, 5]triazinones of the general formula (I)

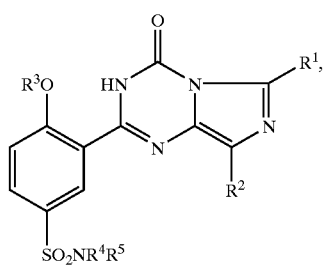

(I)

in which
R$^1$ represents straight-chain or branched alkyl having up to 4 carbon atoms,
R$^2$ represents straight-chain or branched alkyl having up to 4 carbon atoms or represents (C$_3$–C$_8$)-cycloalkyl,
R$^3$ represents hydrogen or straight-chain or branched alkyl having up to 4 carbon atoms, R$^4$ and R$^5$ are identical or different and represent hydrogen, (C$_1$–C$_6$)-alkoxy or hydroxyl or represent (C$_1$–C$_8$)-alkyl which is optionally substituted, up to 3 times, identically or differently, by hydroxyl or (C$_1$–C$_6$)-alkoxy or by radicals of the formulae

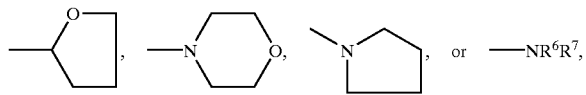

in which
R$^6$ and R$^7$ are identical or different and denote hydrogen or (C$_1$–C$_6$)-alkyl,
and/or, for its part, (C$_1$–C$_8$)-alkyl is optionally substituted by phenyl or phenoxy which, for their part, are optionally substituted, once to three times, identically or differently, by halogen, hydroxyl, (C$_1$–C$_6$)-alkoxy or (C$_1$–C$_6$)-alkyl or by a radical of the formula —SO$_2$NR$^8$R$^9$, in which
R$^8$ and R$^9$ are identical or different and denote hydrogen or (C$_1$–C$_6$)-alkyl, or
R$^4$ represents hydrogen or methyl,
and
R$^5$ represents radicals of the formulae

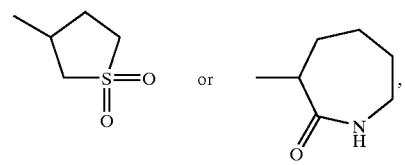

or
represents phenyl which is optionally substituted, up to 3 times, identically or differently, by halogen, acetyl or (C$_1$–C$_6$)-alkoxy or by radicals of the formulae

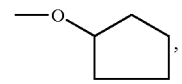

—NR$^{10}$R$^{11}$ or —CH$_2$—P(O)(OR$^{12}$)(OR$^{13}$)
in which
R$^{10}$ and R$^{11}$ are identical or different and denote hydrogen or (C$_1$–C$_4$)-alkyl,
R$^{12}$ and R$^{13}$ are identical or different and denote hydrogen or (C$_1$–C$_6$)-alkyl, or
R$^4$ and R$^5$, together with the nitrogen atom to which they are bonded, form radicals of the formulae

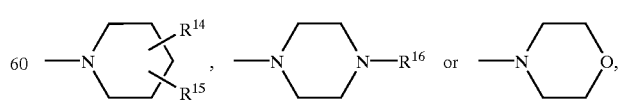

in which
R$^{14}$ and R$^{15}$ are identical or different and denote hydroxyl, hydrogen or (C$_1$–C$_4$)-alkyl which is optionally substituted by hydroxyl, or $R^{14}$ denotes hydrogen, and $R^{15}$ denotes a radical of the formula

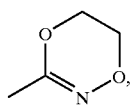

or $R^{14}$ and $R^{15}$ together form a radical of the formula =N—O—CH₃, $R^{16}$ denotes hydrogen or $(C_1-C_6)$-alkyl which is optionally substituted by hydroxyl, or denotes a 5-to 6-membered, aromatic heterocycle having up to 3 heteroatoms from the series S, N and/or O, and the salts, N-oxides and isomeric forms thereof.

The compounds according to the invention can exist in stereoisomeric forms which either relate to each other as image and mirror image (enantiomers) or which do not relate to each other as image and mirror image (diastereomers). The invention relates to both the enantiomers or diastereomers or their respective mixtures. The racemic forms, as well as the diastereomers, can be separated into the stereoisomerically uniform constituents in a known manner.

The substances according to the invention can also be present as salts. Within the context of the invention, preference is given to physiologically harmless salts.

Physiologically harmless salts can be salts of the compounds according to the invention with inorganic or organic acids. Preference is given to salts with inorganic acids, such as hydrochloric acid, hydrobromic acid, phosphoric acid or sulfuric acid, or salts with organic carboxylic or sulfonic acid, such as acetic acid, maleic acid, fumaric acid, malic acid, citric acid, tartaric acid, lactic acid or benzoic acid, or methanesulfonic acid, ethanesulfonic acid, phenylsulfonic acid, toluenesulfonic acid or naphthalenedisulfonic acid.

Physiologically harmless salts can equally well be metal or ammonium salts of the compounds according to the invention. Particular preference is given, for example, to sodium, potassium, magnesium or calcium salts, and also to ammonium salts which are derived from ammonia, or to organic amines, such as ethylamine, di- or triethylamine, di- or triethanolamine, dicyclohexylamine, dimethylaminoethanol, arginine, lysine, ethylenediamine or 2-phenylethylamine.

$(C_3-C_8)$-Cycloalkyl represents cyclopropyl, cyclopentyl, cyclobutyl, cyclohexyl, cycloheptyl or cyclooctyl. Those which may be mentioned as being preferred are: cyclopropyl, cyclopentyl and cyclohexyl.

$(C_1-C_8)$-Alkyl, $(C_1-C_6)$-alkyl and $(C_1-C_4)$-alkyl represents a straight-chain or branched alkyl radical having from 1 to 8, from 1 to 6 and from 1 to 4 carbon atoms, respectively. Those which may be mentioned by way of example are: methyl, ethyl, n-propyl, isopropyl, n-butyl, isobutyl, tert-butyl, n-pentyl and n-hexyl. Preference is given to a straight-chain or branched alkyl radical having from 1 to 4 carbon atoms. Particular preference is given to a straight-chain or branched alkyl radical having from 1 to 3 carbon atoms.

$(C_1-C_6)$-Alkoxy represents a straight-chain or branched alkoxy radical having from 1 to 6 carbon atoms. Those which may be mentioned by way of example are: methoxy, ethoxy, n-propoxy, isopropoxy, n-butoxy, isobutoxy, tert-butoxy, n-pentoxy and n-hexoxy. Preference is given to a straight-chain or branched alkoxy radical having from 1 to 4 carbon atoms. Particular preference is given to a straight-chain or branched alkoxy radical having from 1 to 3 carbon atoms.

Halogen generally represents fluorine, chlorine, bromine and iodine. Preference is given to fluorine, chlorine and bromine. Particular preference is given to fluorine and chlorine.

A 5-to 6-membered aromatic heterocycle having up to 3 heteroatoms from the series S, O and/or N represents, for example, pyridyl, pyrimidyl, pyridazinyl, thienyl, furyl, pyrrolyl, thiazolyl, oxazolyl or imidazolyl. Preference is given to pyridyl, pyrimidyl, pyridazinyl, furyl and thienyl.

Preference is given to compounds according to the invention of the general formula (I), in which $R^1$ represents methyl or ethyl, $R^2$ represents straight-chain or branched alkyl having up to 3 carbon atoms or represents $(C_3-C_6)$-cycloalkyl, $R^3$ represents straight-chain or branched alkyl having up to 3 carbon atoms, $R^4$ and $R^5$ are identical or different and represent hydrogen, $(C_1-C_4)$-alkoxy or hydroxyl or represent $(C_1-C_7)$-alkyl which is optionally substituted, up to 3 times, identically or differently, by hydroxyl or $(C_1-C_4)$-alkoxy or by radicals of the formulae

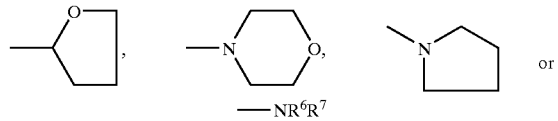

—NR⁶R⁷ in which $R^6$ and $R^7$ are identical or different and denote hydrogen or methyl, and/or, for its part, $(C_1-C_7)$-alkyl is optionally substituted by phenyl or phenoxy which, for their part, are optionally substituted, once to three times, identically or differently, by fluorine, chlorine, hydroxyl, $(C_1-C_4)$-alkoxy or $(C_1-C_4)$-alkyl or by a radical of the formula —SO₂NH₂, or $R^4$ represents hydrogen or methyl, and $R^5$ represents radicals of the formulae

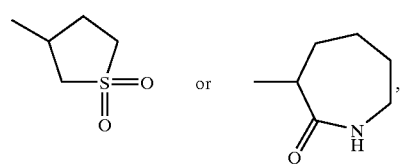

or represents phenyl which is optionally substituted, up to 3 times, identically or differently, by fluorine, chlorine, acetyl or $(C_1-C_4)$-alkoxy or by radicals of the formulae

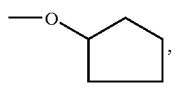

—NR$^{10}$R$^{11}$ or —CH$_2$—P(O)(OR$^{12}$)(OR$^{13}$)

in which
    R$^{10}$ and R$^{11}$ are identical or different and denote hydrogen or methyl,
    R$^{12}$ and R$^{13}$ are identical or different and denote hydrogen or methyl, or
    R$^4$ and R$^5$, together with the nitrogen atom to which they are bonded, form radicals of the formulae

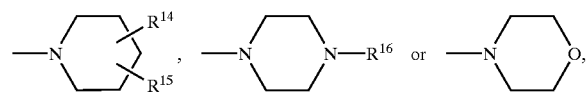

in which
    R$^{14}$ and R$^{15}$ are identical or different and denote hydroxyl, hydrogen or (C$_1$-C$_3$)-alkyl which is optionally substituted by hydroxyl, or
    R$^{14}$ denotes hydrogen, and
    R$^{15}$ denotes a radical of the formula

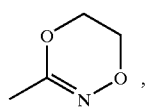

or
    R$^{14}$ and R$^{15}$ together form a radical of the formula =N—O—CH$_3$,
    R$^{16}$ denotes hydrogen or (C$_1$-C$_5$)-alkyl which is optionally substituted by hydroxyl, or denotes pyridyl, pyrimidyl, furyl, pyrryl or thienyl, and the salts, N-oxides and isomeric forms thereof.

Particular preference is given to compounds according to the invention of the general formula (I),
in which
    R$^1$ represents methyl or ethyl,
    R$^2$ represents n-propyl or represents cyclopentyl,
    R$^3$ represents methyl, ethyl or n-propyl,
    R$^4$ and R$^5$ are identical or different and represent hydrogen, (C$_1$-C$_3$)-alkoxy or hydroxyl or represent (C$_1$-C$_6$)-alkyl which is optionally substituted, up to 3 times, identically or differently, by hydroxyl or (C$_1$-C$_3$)-alkoxy or by radicals of the formulae

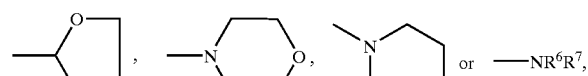

in which
    R$^6$ and R$^7$ are identical or different and denote hydrogen or methyl, and/or, for its part, (C$_1$-C$_6$)-alkyl is optionally substituted by phenyl or phenoxy which, for their part, are optionally substituted, once to three times, identically or differently, by fluorine, hydroxyl or methoxy or by a radical of the formula —SO$_2$NH$_2$, or
    R$^4$ represents hydrogen or methyl,
and
    R$^5$ represents radicals of the formulae

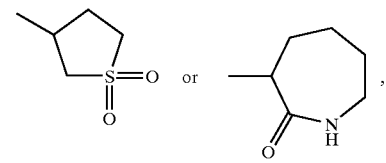

or
    represents phenyl which is optionally substituted, up to 3 times, identically or differently, by fluorine, acetyl or methoxy or by radicals of the formulae

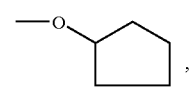

—NR$^{10}$R$^{11}$ or —CH$_2$—R(O)(OR$^{12}$)(OR$^{13}$), in which
    R$^{10}$ and R$^{11}$ are identical or different and denote hydrogen or methyl,
    R$^{12}$ and R$^{13}$ denote methyl, or
    R$^4$ and R$^5$, together with the nitrogen atom to which they are bonded, form radicals of the formulae

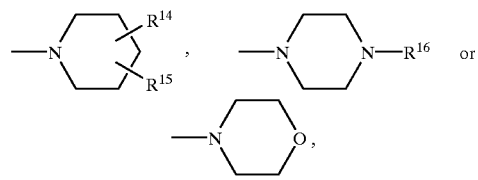

in which
    R$^{14}$ and R$^{15}$ are identical or different and denote hydroxyl, hydrogen or a radical of the formula —(CH$_2$)$_2$—OH, or
    R$^{14}$ denotes hydrogen
and
    R$^{15}$ denotes a radical of the formula

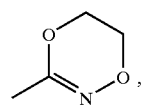

or
    R$^{14}$ and R$^{15}$ together form a radical of the formula =N—O—CH$_3$,
    R$^{16}$ denotes hydrogen, pyrimidyl or a radical of the formula —(CH$_2$)$_2$—OH, and the salts, N-oxides and isomeric forms thereof.
Very particular preference is given to the following compounds according to the invention:
Structure
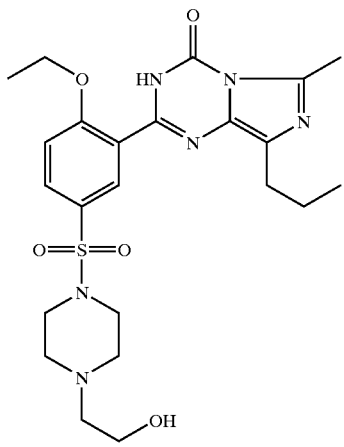
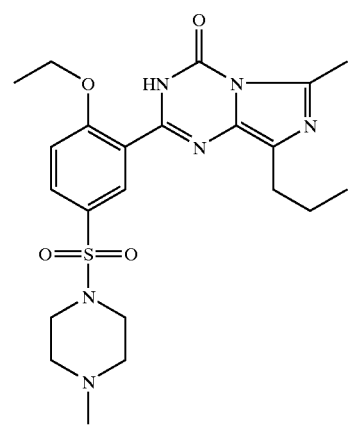
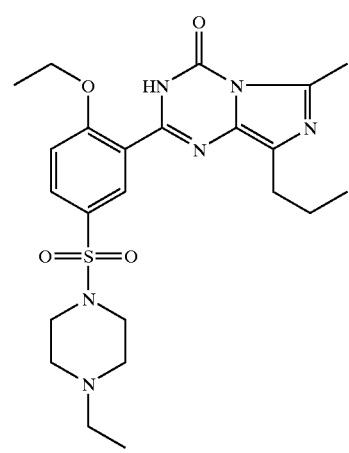
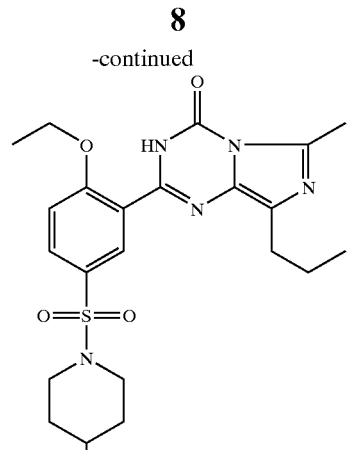
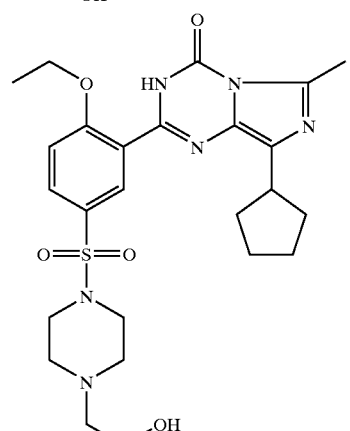
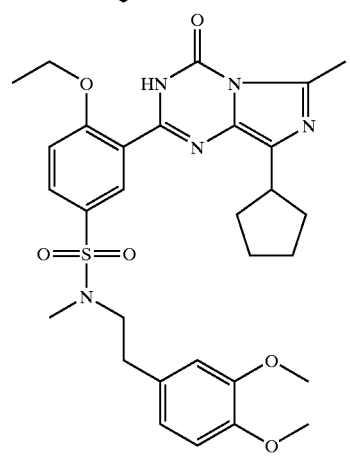
In addition, a process was found for preparing the compounds according to the invention of the general formula (I), in which process compounds of the general formula (II)
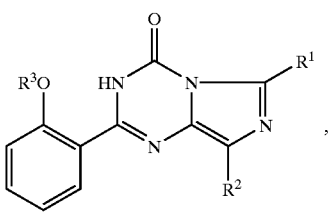
(II)

in which

R¹, R² and R³ have the abovementioned meaning, are first of all converted, by reaction with chlorosulfonic acid (ClSO₃H), where appropriate in inert solvents, where appropriate in the presence of a base, into the compounds of the general formula (III)

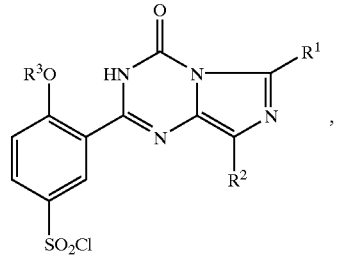

(III)

in which

R¹, R² and R³ have the abovementioned meaning, and, in a last step, are reacted with amines of the general formula (IV)

HN—R⁴R⁵ (IV), in which

R⁴ and R⁵ have the abovementioned meaning.

The process according to the invention can be explained, by way of example, by the following formula scheme:

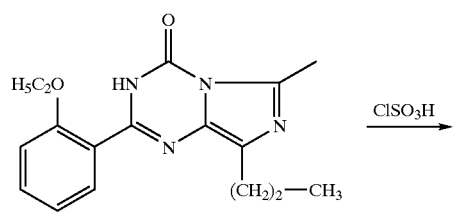
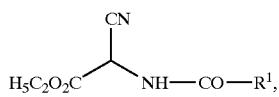

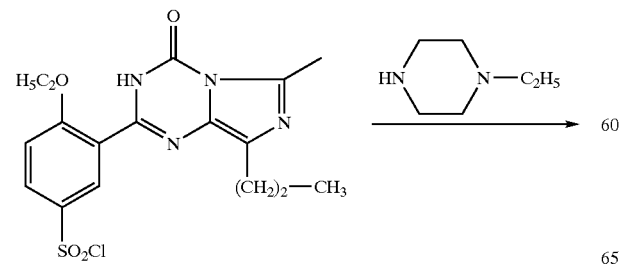

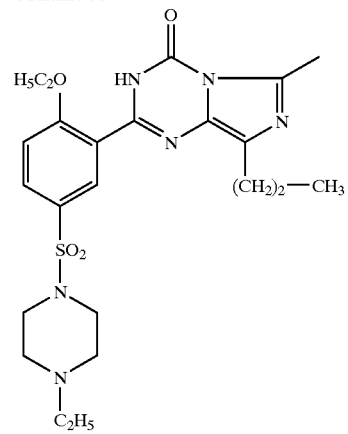

Solvents which are suitable for the individual steps are the customary organic solvents which are not altered under the reaction conditions. These solvents preferably include ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethane, trichloroethylene or chlorobenzene, or ethyl acetate, dimethylformamide, hexamethylphosphoric triamide, acetonitrile, acetone, dimethoxyethane or pyridine. It is likewise possible to use mixtures of the abovementioned solvents.

In general, the reaction temperatures can vary over a relatively wide range. In general, the temperatures employed are in a range of from −20° C. to 200° C., preferably of from 0° C. to 70° C.

In general, the process steps according to the invention are carried out under standard pressure. However, it is also possible to carry them out under positive pressure or under negative pressure (e.g. in a range from 0.5 to 5 bar).

The reactions can, for example, take place in a temperature range of from 0° C. to room temperature and under standard pressure.

The compounds of the general formula (II) are novel and can be prepared by reacting compounds of the general formula (V)

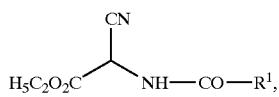

(V)

in which
R¹ has the abovementioned meaning,
in the NaOC₂H₅/C₂H₅OH system, with compounds of the general formula (VI)

R²-halogen (VI), in which
R² has the abovementioned meaning,
to give the compounds of the general formula (VII)

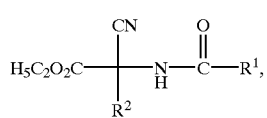

(VII)

in which
R¹ and R² have the abovementioned meaning,
and subsequently, likewise in the NaO₂H₅/C₂H₅OH system, carrying out a reaction with compounds of the general formula (VIII)

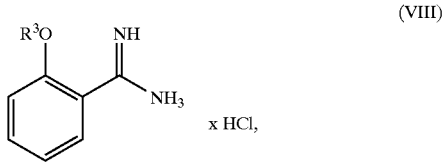

(VIII)

in which
R³ has the abovementioned meaning,
to give the compounds of the general formula (IX)

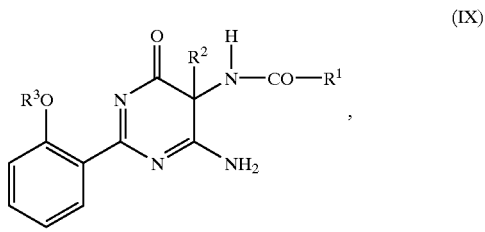

(IX)

in which
R¹, R² and R³ have the abovementioned meaning,
and finally cyclizing in inert solvents, in the presence of hexamethyldisilazane (HMDS) and chlorotrimethylsilane (TMSCl).

Solvents which are suitable for the individual steps are the customary organic solvents which are not altered under the reaction conditions. These solvents preferably include ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethane, trichloroethylene or chlorobenzene, or ethyl acetate, dimethylformamide, hexamethylphosphoric triamide, acetonitrile, acetone, dimethoxyethane or pyridine. It is likewise possible to use mixtures of the abovementioned solvents.

In general, the reaction temperatures can vary within a relatively wide range. In general, the temperatures employed are in a range from −20° C. to 200° C., preferably of from 0° C. to 70° C.

The process steps according to the invention are generally carried out under standard pressure. However it is also possible to carry them out under positive pressure or under negative pressure (e.g. in a range from 0.5 to 5 bar).

The reactions can, for example, take place in a temperature range of from 0° C. to room temperature and under standard pressure.

The compounds of the general formula (III) are novel and can be prepared as described above.

The compounds of the general formulae (IV), (V), (VI), (VII) and (VIII) are either known per se or can be prepared using customary methods.

Some of the compounds of the general formula (IX) are novel and can be prepared using customary methods.

The compounds according to the invention of the general formula (I) exhibit a valuable pharmacological spectrum of activity which it was not possible to foresee.

They inhibit either one or several of the c-GMP-metabolizing phosphodiesterases (PDE I, PDE II and PDE V). This leads to an increase in c-GMP. The differing expression of the phosphodiesterases in different cells, tissues and organs, as well as the differing subcellular location of these enzymes, make it possible, in combination with the selective inhibitors according to the invention, to address the different cGMP-regulated processes selectively.

In addition, the compounds according to the invention augment the effect of substances such as EDRF (endothelium-derived relaxing factor) and ANP (atrial natriuretic peptide), of nitro vasodilators and all other substances which increase the concentration of the cGMP in another way than phosphodiesterase inhibitors.

The compounds according to the invention of the general formula (I) are therefore suitable for the prophylaxis and/or treatment of diseases in which an increase in the concentration of cGMP is therapeutic, i.e. diseases which are connected with cGMP-regulated processes (in English, usually simply termed cGMP-related diseases). These diseases include cardiovascular diseases, diseases of the urogenital system and cerebrovascular diseases.

Within the meaning of the present invention, the term "cardiovascular diseases" covers diseases such as high blood pressure, neuronal hypertension, stable and unstable angina, peripheral and cardiac vascular diseases, arrhythmias, thromboembolic diseases and ischemias such as myocardial infarction, stroke, transistory and ischemic attacks, angina pectoris and peripheral circulatory disturbances, and also prevention of restenoses following thrombolysis therapy, percutaneous transluminal angioplasty (PTA), percutaneous transluminal coronary angioplasties (PTCA) and bypass.

Furthermore, the compounds according to the invention of the general formula (I) can also have importance for cerebrovascular diseases. These include, for example, cerebral ischemia, stroke, reperfusion damage, brain trauma, edemas, cerebral thromboses, dementia and Alzheimer's disease.

The relaxing effect on smooth musculature makes them suitable for treating disorders of the urogenital system such as prostate hypertrophy and incontinence and also, in particular, for treating erectile dysfunction and female sexual dysfunction.

Activity of the Phosphordiesterases (PDEs)

The cGMP-stimulatable PDE II, the cGMP-inhibitable PDE III and the cAMP-specific PDE IV were isolated either from porcine heart myocardium or from bovine heart myocardium. The Ca²⁺-calmodulin-stimulatable PDE I was isolated from porcine aorta, porcine brain or, preferably, from bovine aorta. The c-GMP-specific PDE V was obtained from porcine small intestine, porcine aorta, human blood platelets and, preferably, from bovine aorta. Purification was effected by means of anion exchange chromatography on Pharmacia MonoQ^R, essentially in accordance with the method described by M. Hoey and Miles D. Houslay, Biochemical Pharmacology, Vol. 40, 193–202 (1990) and C. Lugman et al. Biochemical Pharmacology Vol. 35 1743–1751 (1986).

The enzyme activity is determined in a 100 µl test mixture, in 20 mM Tris/HCl buffer pH 7.5, which contains 5 mM MgCl₂, 0.1 mg of bovine serum albumin/ml and either 800 Bq of ³HcAMP or ³HcGMP. The final concentration of the corresponding nucleotides is 10⁻⁶ mol/l. The reaction is started by adding the enzyme, with the quantity of enzyme being measured such that approx. 50% of the substrate is transformed during the incubation time of 30 min. In order to test the cGMP-stimulatable PDE II, ³HcAMP is used as the substrate and 10⁻⁶ mol of unlabeled cGMP/l is added to the mixture. In order to test the $Ca^{2+}$-calmodulin-dependent PDE I, 1 μM $CaCl_2$ and 0.1 μM calmodulin are additionally added to the reaction mixture. The reaction is stopped by adding 100 μl of acetonitrile which contains 1 mM cAMP and 1 mM AMP. 100 μl of the reaction mixture are separated by HPLC and the cleavage products are determined quantitatively online using a flow-through scintillation counter. The substance concentration at which the reaction rate is decreased by 50% is measured. The "phosphodiesterase [$^3$H] cAMP-SPA enzyme assay" and the "phosphodiesterase [$^3$H] cGMP-SPA enzyme assay", supplied by Amersham Life Science, were additionally used for testing. The test was carried out using the experimental protocol specified by the manufacturer. The [$^3$H] cAMP-SPA assay was used for determining the activity of PDE II, with $10^{-6}$ M cGMP being added to the reaction mixture for the purpose of activating the enzyme. $10^{-7}$ M calmodulin and 1 μM $CaCl_2$ were added to the reaction mixture for the purpose of measuring PDE I. PDE V was measured using the [3 H] cGMP-SPA assay.

In principle, the inhibition of one or more phosphodiesterases of this type leads to an increase in the concentration of cGMP. As a result, the compounds are of interest for all therapies in which an increase in the concentration of cGMP can be assumed to be therapeutic.

The investigation of the cardiovascular effects was carried out on normotensive rats and on SH rats and on dogs. The substances were administered intravenously or orally.

The examination for erection-inducing effects was carried out on conscious rabbits [H. Naganuma, T. Egashira, J. Fuji, Clinical and Experimental Pharmacology and Physiology 20, 177–183 (1993)]. The substances were administered orally or parenterally.

The novel active compounds, and also their physiologically harmless salts (e.g. hydrochlorides, maleates or lactates) can be converted, in a known manner, into the customary formulations, such as tablets, coated tablets, pills, granules, aerosols, syrups, emulsions, suspensions and solutions, using inert, nontoxic, pharmaceutically suitable carrier substances or solvents. In this connection, the therapeutically effective compound should in each case be present at a concentration of from about 0.5 to 90% by weight of the total mixture, i.e. in quantities which are sufficient for achieving the specified dosage range.

The formulations are prepared, for example, by extending the active compounds with solvents and/or carrier substances, where appropriate using emulsifiers and/or dispersants, with it being possible, for example when using water as a diluent, to use organic solvents as auxiliary solvents, where appropriate.

The administration is effected in a customary manner, preferably orally, transdermally or parenterally, for example perlingually, by the buccal route, intravenously, nasally, rectally or by inhalation.

For use in humans, doses of from 0.001 to 50 mg/kg, preferably 0.01 mg/kg–20 mg/kg, are generally administered when administering orally. A dose of 0.001 mg/kg–0.5 mg/kg is expedient when administering parenterally, for example by way of mucosae, nasally, by the buccal route or by inhalation.

Despite this, it can be necessary, where appropriate, to depart from the abovementioned quantities, specifically in dependence on the body weight or the nature of the route of administration, on the individual response to the medicament, on the nature of its formulation and on the time or interval at which the administration takes place. Thus, it can in some cases be sufficient to make do with less than the abovementioned smallest quantity whereas, in other cases, the abovementioned upper limit has to be exceeded. When relatively large quantities are being administered, it may be advisable to divide up these quantities into several individual doses which are given during the course of the day.

The compounds according to the invention are also suitable for use in veterinary medicine. For uses in veterinary medicine, the compounds, or their nontoxic salts, can be administered in a suitable formulation, in accordance with common veterinary procedures. The veterinarian can establish the nature of the application, and the dose, in accordance with the nature of the animal to be treated.

In the following examples of preparing the precursors and end products, it is always necessary, in structural formulae containing one or more unsaturated valences on the nitrogen atom or oxygen atom, to add a hydrogen.

In other words, in structures containing, for example, a structural element "—N—", what is meant is actually "—NH—", and in structures containing, for example, a structural element "—O", what is meant is actually "—OH".

Preparing the Precursors

EXAMPLE I

Ethyl 2-acetylamino-2-cyanopentanoate

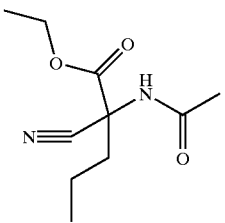

1.35 g of sodium (58.8 mmol) are dissolved in 200 ml of ethanol and the resulting solution is cooled down to 0° C. 10 g (58.8 mmol) of ethyl acetamidocyanoacetate are added. After a clear solution has formed, a solution of 7.23 g (58.8 mmol) of bromopropane in 10 ml of ethanol is added dropwise and the reaction mixture is stirred at room temperature for 2 hours. A solution of 7.23 g (58.8 mmol) of bromopropane in 10 ml of ethanol is added once again and the reaction mixture is heated under reflux for 16 hours. The solvent is removed in vacuo and the residue is taken up in dichloromethane; the solution is washed with water and dried over magnesium sulfate. The solvent is removed in vacuo and the residue is stirred up with petroleum ether. After filtering off with suction, 7.5 g (60%) of ethyl 2-acetylamino-2-cyanopentanoate are obtained.

200 MHz $^1$H-NMR ($CDCl_3$): 1.00, t, 3H; 1.36, t, 3H; 1.51, m, 2H; 2.08, m, 5H; 4.34, q, 2H; 6.45, s, broad, 1H.

EXAMPLE II

2-Ethoxy-benzonitrile

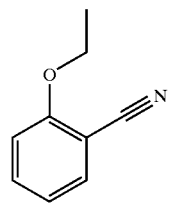

25 g (210 mmol) of 2-hydroxylbenzonitrile are heated, together with 87 g of potassium carbonate and 34.3 g (314.8 mmol) of ethyl bromide, in 500 ml of acetone under reflux overnight. The solid is filtered off, the solvent is removed in vacuo and the residue is distilled in vacuo. 30.0 g (97%) of a colorless liquid are obtained.

200 MHz $^1$H-NMR (DMSO-D$_6$): 1.48, t, 3H; 4.15, quart., 2H; 6.99, dt, 2H; 7.51, dt, 2H.

EXAMPLE III

2-Ethoxy-benzamidine hydrochloride

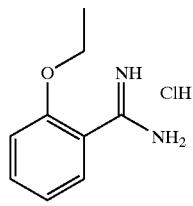

21.4 g (400 mmol) of ammonium chloride are suspended in 375 ml of toluene and the suspension is cooled down to 0° C. 200 ml of a 2 M solution of trimethylaluminum in hexane are added dropwise and the mixture is stirred at room temperature until the evolution of gas has come to an end. After 29.44 g (200 mmol) of 2-ethoxybenzonitrile (example II) have been added, the reaction mixture is stirred overnight at 80° C. (bath).

Having been cooled down, the reaction mixture is added, while cooling with ice, to a suspension consisting of 100 g of silica gel and 950 ml of chloroform and the mixture is stirred at room temperature for 30 minutes. Filtration with suction is carried out and the subsequent washing takes place with the same quantity of methanol. The mother liquor is evaporated and the resulting residue is stirred up with a mixture of dichloromethane and methanol (9:1), after which the solid is filtered off with suction and the mother liquor is evaporated. 3.4 g (76%) of a colorless solid are obtained.

200 MHz $^1$H-NMR (DMSO-D$_6$): 1.36, t, 3H; 4.12, quart., 2H; 7.10, t, 1H; 7.21, d, 1H; 7.52, m, 2H; 9.30, s, broad, 4H.

EXAMPLE IV

N-[6-Amino-2-(2-ethoxyphenyl)-4-oxo-5-propyl-4,5-dihydro-pyrimidin-5-yl]-acetamide

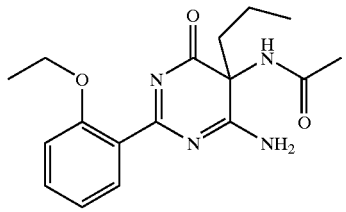

33 g of 2-ethoxybenzamidine hydrochloride (example III) are added to a solution of 3.97 g of sodium in 1300 ml of ethanol and the reaction mixture is stirred at room temperature for 45 minutes. The reaction mixture is filtered and the filtrate is added to a solution of 69.8 g (329 mmol) of ethyl 2-acetylamino-2-cyanopentanoate (example I) in 800 ml of ethanol and the mixture is heated under reflux for 4 hours. The solvent is removed in vacuo and the residue is taken up in dichloromethane; the organic phase is shaken with water and sodium chloride solution and dried over sodium sulfate and the solvent is removed in vacuo. Chromatographic purification (dichloromethane/methanol) yields 11.57 g (21%) of N-[6-amino-2-(2-ethoxyphenyl)-4-oxo-5-propyl-4,5-dihydro-pyriminin-5-yl]-acetamide.

200 MHz $^1$H-NMR (CDCl$_3$): 0.91, t, 3H; 1.41, m, 2H; 1.58, t, 3H; 2.07, m, 5H; 4.39, q, 2H; 7.08, m, 3H; 7.53, dt, 1H; 8.41, dd, 1H.

EXAMPLE V 2-(2-Ethoxyphenyl)-6-methyl-8-propyl-3H-imidazo[1,5-α][1,3,5]triazin-4-one

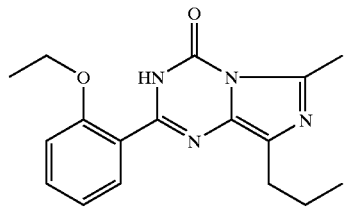

11.41 g (105 mmol) of chlorotrimethylsilane are added to a solution of 11.57 g (35 mmol) of N-[6-amino-2-(2-ethoxyphenyl)-4-oxo-5-propyl4,5-dihydro-pyriminin-5-yl]-acetamide (example IV) in 500 ml of pyridine and the reaction mixture is stirred at room temperature for 20 minutes. After 16.96 g (105 mmol) of hexamethyldisilazane have been added, the reaction mixture is heated under reflux for 16 hours. The solvent is removed in vacuo and the residue is taken up in dichloromethane; the solution is extracted with water and 1 N HCl and dried over magnesium sulfate, after which the solvent is removed in vacuo. The residue is stirred up with ether and the solid residue is purified chromatographically (cyclohexane/ethyl acetate). 1.655 g (15%) of solid are obtained.

200 MHz $^1$H-NMR (CDCl$_3$): 1.02, t, 3H; 1.61, t, 3H; 1.80, hex, 2H; 2.80, t, 2H; 2.88, s, 3H, 4.30, q, 2H; 7.05, d, 1H; 7.15, t, 1H; 7.58, dt, 1H; 8.39, dd, 1H; 10.35, s, broad, 1H.

EXAMPLE VI

4-Ethoxy-3-(6-methyl-4-oxo-8-propyl-3,4-dihydro-imidazo[1,5-α][1,3,5]triazin-2-yl)-benzenesulfonyl chloride

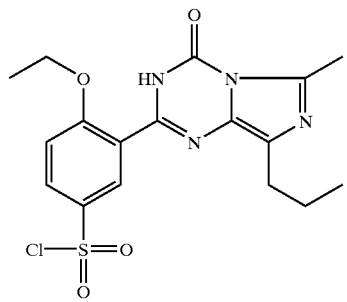

1.64 g (5.25 mmol) of 2-(2-ethoxyphenyl)-6-methyl-8-propyl-3H-imidazo[1,5-α][1,3,5]triazin-4-one (example VI) are added in portions to 3.14 ml of chlorosulfonic acid while cooling with ice. The reaction mixture is stirred at room temperature for 16 hours, then diluted with dichloromethane and poured onto ice water. The organic phase is washed with water and dried over magnesium sulfate and the solvent is removed in vacuo. 2.15 g (99%) of 4-ethoxy-3-(6-methyl-4-oxo-8-propyl-3,4-dihydro-imidazo[1,5-α][1,3,5]triazin-2-yl)-benzene-sulfonyl chloride are obtained.

200 MHz $^1$H-NMR (CDCl$_3$):0.92, t, 3H; 1.34, t, 3H; 1.71, hex, 2H; 2.80, t, 2H; 2.96, s, 3H; 4.15, q, 2H; 7.12, d, 1H; 7.73, dd, 1H; 7.81, d, 1H; 12.5, s, broad, 1H.

EXAMPLE VII

Ethyl 2-acetylamino-2-cyano-2-cyclopentylethanoate

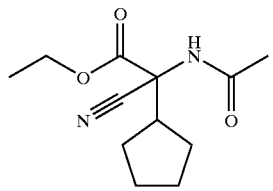

125 g of ethyl acetamidocyanoacetate (734.6 mmol) are added, at room temperature, to a solution of 17.74 g of sodium (771.3 mmol) in 1.2 of ethanol. After a clear solution has been formed, 157.5 ml of cyclopentyl bromide (1.47 mol) are added dropwise. The mixture is stirred overnight under reflux and then concentrated on a rotary evaporator. The residue is taken up in dichloromethane and the solution is washed twice with water, dried over magnesium sulfate and concentrated. The crystalline residue is stirred up with ether and filtered off with suction.

Yield: 70.8 g (40.4% of theory)

MS (DCI, $NH_3$): m/z (%)=256 (M+$H_2O$) (100)

$^1$H-NMR (200 MHz, $CDCl_3$): δ=1.35 (t, 3 H); 1.55–1.82 (m, 7 H); 1.91–2.03 (m, 1 H); 2.06 (s, 3 H); 2.37–2.50 (m, 1 H); 4.31 (q, 2 H); 6.79 (s, 1 H).

EXAMPLE VIII

N-[6-Amino-5-cyclopentyl-2-(2-ethoxyphenyl)-4-oxo-4,5-dihydropyrimidin-5-yl]acetamide

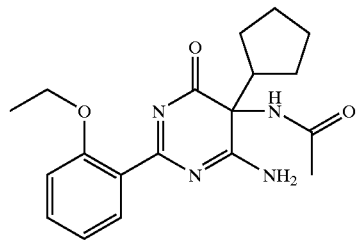

5.02 g (25 mmol) of 2-ethoxybenzamidine hydrochloride (example III) are added to a solution of 0.6 g of sodium (26.25 mmol) in 80 ml of ethanol. After 45 min at room temperature, the resulting mixture is filtered into a solution of 11.91 g (50 mmol) of ethyl 2-acetylamino-2-cyano-2-cyclopentylethanoate in 120 ml of ethanol and the mixture is subsequently stirred under reflux for 5 h. It is then concentrated and the residue is taken up in dichloromethane; the solution is washed twice with water, dried and evaporated. The crude product is purified by column chromatography on silica gel using dichloromethane/methanol 9:1.

Yield 545.4 mg (6.1% of theory)

MS (DCI, $NH_3$): m/z (%)=357 (M+H), (100)

$^1$H-NMR (200 MHz, $CDCl_3$): δ=1.45–1.90 (m, 12 H); 2.05 (s, 3 H); 2.42–2.58 (m, 1 H); 4.28 (q, 2 H); 6.99–7.14 (m, 2 H); 7.19 (s, 1 H); 7.53 (dt, 1 H); 8.87 (dd, 1 H).

EXAMPLE IX

8-Cyclopentyl-2-(2-ethoxy-phenyl)-6-methyl-3H-imidazo[1,5-α][1,3,5]triazin-4-one

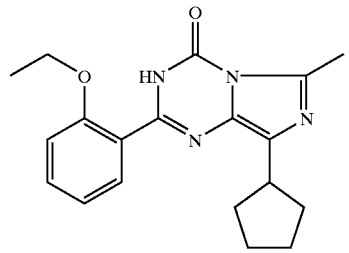

1,6 g (4.5 mmol) of N-[6-amino-5-cyclopentyl-2-(2-ethoxyphenyl)-4-oxo-4,5-dihydropyrimidin-5-yl]acetamide (example VIII) are initially introduced in 64 ml of anhydrous pyridine. 1.71 ml (13.5 mmol) of chlorotrimethylsilane are added dropwise and the mixture is subsequently stirred at room temperature for 20 min. After 2.8 ml (13.5 mmol) of hexamethyldisilazane have been added, the mixture is subsequently stirred overnight under reflux. It is then evaporated down to dryness and the residue is taken up in 80 ml of methanol; the solution is stirred at room temperature for 45 min. It is then evaporated and the residue is purified by flash chromatography using cyclohexane/ethyl acetate 1:1.

Yield 727 mg (47.5% of theory)

MS (DCI, $NH_3$): m/z (%) =339 (M+H) (100)

$^1$H-NMR (200 MHz, $CDCl_3$): δ=1.60 (t, 3 H); 1.65–2.12 (m, 8 H); 2.89 (s, 3 H); 3.40 (qui, 1 H); 4.29 (q, 2 H); 7.0–7.18 (m, 2 H); 7.49 (dt, 1 H); 8.48 (dd, 1 H); 10.31 (bs, 1 H).

EXAMPLE X

4-Ethoxy-3-(8-cyclopentyl-6-methyl-4-oxo-3,4-dihydro-imidazol[1,5-α][1,3,5]-triazin-2-yl)-benzenesulfonyl chloride

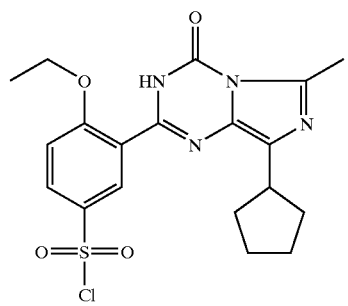

372.3 mg (1.1 mmol) of 8-cyclopentyl-2-(2-ethoxy-phenyl)-6-methyl-3H-imidazo [1,5-α][1,3,5]triazin-4-one (example IX) are added in portions to 0.66 ml (9.9 mmol) of ice-cooled chlorosulfonic acid. The mixture is subsequently stirred overnight at room temperature before being diluted with dichloromethane and poured onto ice water. The organic phase is separated off. The aqueous phase is extracted once again with dichloromethane and the organic phases are combined, dried and evaporated.

Yield 266.5 mg (55.5% of theory)

$^1$H-NMR (200 MHz, $CDCl_3$): δ=1.69 (t, 3 H); 1.70–2.14 (m, 8 H); 3.49–3.51 (m. 1 H); 4.45 (q, 2 H); 7.24 (d, 1 H); 8.11 (s, 1 H); 9.04 (d, 1 H); 9.89 (bs, 1 H).

Preparing the Active Compounds

EXAMPLE 1
2-{2-Ethoxy-5-[4-(2-hydroxy-ethyl)-piperazine-1-sulfonyl]-phenyl}-6-methyl-8-propyl-3H-imidazo[1,5-α][1,3,5]triazin-4-one

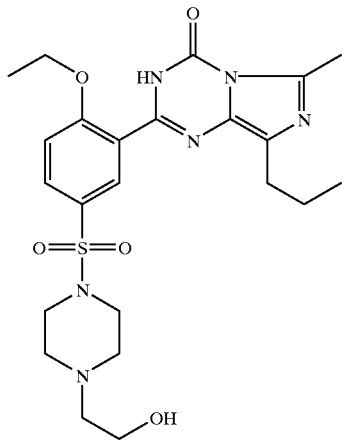

86 mg (0.66 mmol) of hydroxylethylpiperazine are added to a solution of 90 mg (0.22 mmol) of 4-ethoxy-3-(6-methyl-4-oxo-8-propyl-3,4-dihydro-imidazo[1,5-α][1,3,5]triazin-2-yl)-benzenesulfonyl chloride (example VI) in 5 ml of dichloromethane and the reaction mixture is stirred at room temperature for 16 hours. After chromatographic purification (dichloromethane/methanol=95:5), 63 mg (57%) of 2-{2-ethoxy-5-[4-(2-hydroxy-ethyl)-piperazine-1-sulfonyl]-phenyl}-6-methyl-8-propyl-3H-imidazo[1,5-α][1,3,5]triazin-4-one are obtained.

400 MHz $^1$H-NMR (CDCl$_3$): 1.00, t, 3H; 1.65, t, 3H; 1.79, hex, 2H; 1.90, s, broad, 1H; 2.56, t, 2H; 2.63, m, 4H; 2.80, t, 2H; 2.87, s, 3H; 3.09, s, broad, 4H; 3.58, m, 2H; 4.39, q, 2H; 7.16, d, 1H; 7.82, dd, 1H; 8.70, d, 1H; 10.0, s, broad, 1H.

EXAMPLE 2
2-[2-Ethoxy-5-(4-methyl-piperazine-1-sulfonyl)-phenyl]-6-methyl-8-propyl-3H-imidazo[1,5-α][1,3,5]triazin-4-one

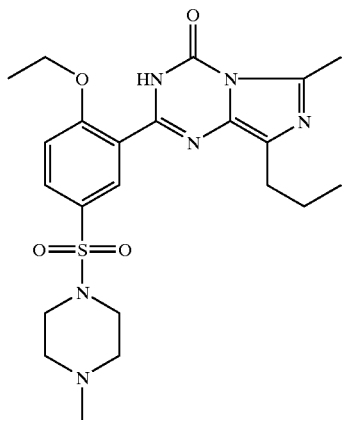

73 mg (0.73 mmol) of N-methylpiperazine are added to a solution of 100 mg (0.24 mmol) of 4-ethoxy-3-(6-methyl-4-oxo-8-propyl-3,4-dihydro-imidazo[1,5-α][1,3,5]triazin-2-yl)-benzenesulfonyl chloride (example VI) in 5 ml of dichloromethane and the reaction mixture is stirred at room temperature for 2 hours. After chromatographic purification (dichloromethane/methanol=95:5), 110 mg (95%) of 2-[2-ethoxy-5-(4-methyl-piperazine-1-sulfonyl)-phenyl]-6-methyl-8-propyl-3H-imidazo[1,5-α][1,3,5]triazin-4-one are obtained.

200 MHz $^1$H-NMR (CDCl$_3$): 1.00, t, 3H; 1.65, t, 3H; 1.79, hex, 2H; 2.29, s, 3H; 2.50, m, 4H; 2.80, t, 2H; 2.89, s, 3H; 3.10, m, 4H; 4.37, q, 2H; 7.13, d, 1H; 7.83, dd, 1H; 8.71, dd, 1H; 10.0, s, broad, 1H.

EXAMPLE 3
2-[2-Ethoxy-5-(4-ethyl-piperazine-1-sulfonyl)-phenyl]-6-methyl-8-propyl-3H-imidazo[1,5-α][1,3,5]triazin-4-one

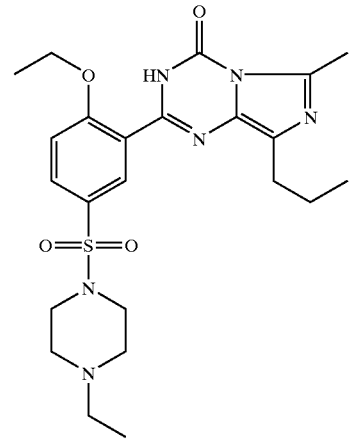

83 mg (0.73 mmol) of N-ethylpiperazine are added to a solution of 100 mg (0.24 mmol) of 4-ethoxy-3-(6-methyl-4-oxo-8-propyl-3,4-dihydro-imidazo[1,5-α]-[1,3,5]triazin-2-yl)-benzenesulfonyl chloride (example VI) in 5 ml of dichloromethane and the reaction mixture is stirred at room temperature for 2 hours. After chromatographic purification (dichloromethane/methanol=95:5), 104 mg (87%) of 2-[2-ethoxy-5-(4-ethyl-piperazine-1-sulfonyl)-phenyl]-6-methyl-8-propyl-3H-imidazo[1,5-α][1,3,5]triazin-4-one are obtained.

200 MHz $^1$H-NMR (CDCl$_3$): 1.00, t, 3H; 1.05, t, 3H; 1.65, t, 3H; 1.79, hex, 2H; 2.42, q, 2H; 2.54, m, 4H; 2.78, t, 2H; 2.87, s, 3H; 3.09, m, 4H; 4.37, q, 2H; 7.13, d, 1H; 7.83, dd, 1H; 8.71, dd, 1H; 10.0, s, broad, 1H.

EXAMPLE 4
N-[2-(3,4-Dimethoxy-phenyl)-ethyl]-4-ethoxy-N-methyl-3-(6-methyl-4-oxo-8-propyl-3,4-dihydro-imidazo[1,5-α][1,3,5]triazin-2-yl)-benzenesulfonamide

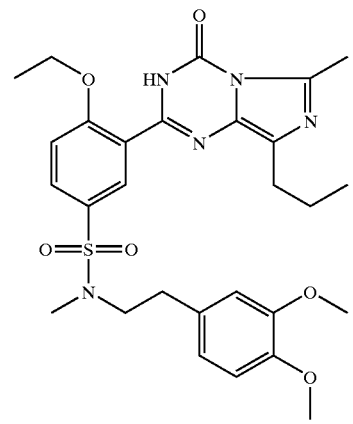

143 mg (0.73 mmol) of N-(3,4-dimethoxyphenylethyl)-N-methylamine are added to a solution of 100 mg (0.24 mmol) of 4-ethoxy-3-(6-methyl-4-oxo-8-propyl-3,4-dihydro-imidazo[1,5-α][1,3,5]triazin-2-yl)-benzenesulfonyl chloride (example VI) in 5 ml of dichloromethane and the reaction mixture is stirred at room temperature for 2 hours. After chromatographic purification (dichloromethane/methanol=

95:5), 138 mg (98%) of N-[2-(3,4-dimethoxy-phenyl)-ethyl]-4-ethoxy-N-methyl-3-(6-methyl-4-oxo-8-propyl-3,4-dihydro-imidazo[1,5-α][1,3,5]triazin-2-yl)-benzenesulfonamide are obtained.

200 MHz ¹H-NMR (CDCl₃): 0.95, t, 3H; 1.62, t, 3H; 1.78, hex, 2H, 2.83, m, 10H; 3.31, t, 2H; 3.85, s, 6H; 4.35, q, 2H; 6.72, m, 3H; 7.09, d, 1H; 7.81, dd, 1H; 8.73, d, 1H; 10.0, s, broad, 1H.

EXAMPLE 5

4-Ethoxy-N-(2-methoxy-ethyl)-3-(6-methyl-4-oxo-8-propyl-3,4-dihydro-imidazo[1,5-α][1,3,5]triazin-2-yl)-benzenesulfonamide

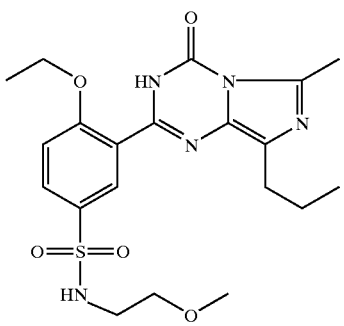

55 mg (0.73 mmol) of 2-methoxyethylamine are added to a solution of 100 mg (0.24 mmol) of 4-ethoxy-3-(6-methyl-4-oxo-8-propyl-3,4-dihydro-imidazo[1,5-α][1,3,5]triazin-2-yl)-benzenesulfonyl chloride (example VI) in 5 ml of dichloromethane and the reaction mixture is stirred at room temperature for 2 hours. After chromatographic purification (dichloromethane/methanol=95:5) and stirring up with diethyl ether, 64 mg (57%) of 4-ethoxy-N-(2-methoxy-ethyl)-3-(6-methyl-4-oxo-8-propyl-3,4-dihydro-imidazo[1,5-α][1,3,5]triazin-2-yl)-benzenesulfonamide are obtained.

200 MHz ¹H-NMR (CDCl₃): 1.01, t, 3H; 1.65, t, 3H; 1.80, hex, 2H, 2.80, t, 2H; 2.88, s, 3H; 3.18, t, 2H; 3.30, s, 3H; 3.46, t, 2H; 4.38, q, 2H; 7.13, d, 1H; 7.95, dd, 1H; 8.85, d, 1H, 10.02, s, broad, 1H.

EXAMPLE 6

2-[2-Ethoxy-5-(4-hydroxyl-piperidine-1-sulfonyl)-phenyl]-6-methyl-8-propyl-3H-imidazo[1,5-α][1,3,5]triazin-4-one

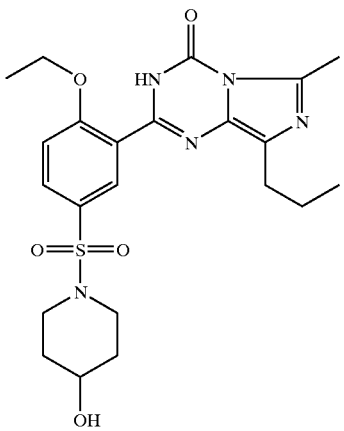

74 mg (0.73 mmol) of 4-hydroxylpiperidine are added to a solution of 100 mg (0.24 mmol) of 4-ethoxy-3-(6-methyl-4-oxo-8-propyl-3,4-dihydro-imidazo[1,5-α][1,3,5]triazin-2-yl)-benzenesulfonyl chloride (example VI) in 5 ml of dichloromethane and the reaction mixture is stirred at room temperature for 2 hours. After chromatographic purification (dichloromethane/methanol=95:5), 100 mg (87%) of 2-[2-ethoxy-5-(4-hydroxyl-piperidine-1-sulfonyl)-phenyl]-6-methyl-8-propyl-3H-imidazo[1,5-α][1,3,5]triazin4-one are obtained.

200 MHz ¹H-NMR (CDCl₃): 1.01, t, 3H; 1.65, m, 9H; 2H, 2.78, t, 2H; 2.88, s, 3H; 3.00, m 2H; 3,30, m, 2H; 3.83, s, 1H; 4.38, q, 2H, 7.15, d, 1H, 7.85, dd, 1H, 8.73, d, 1H, 10.02, s, broad, 1H.

EXAMPLE 7

N-(N-Hydroxyethyl-piperazinyl)-[4-ethoxy-3-(8-cyclopentyl-6-methyl-4-oxo-3,4-dihydro-imidazol[1,5-α][1,3,5]triazin-2-yl]-benzenesulfonamide

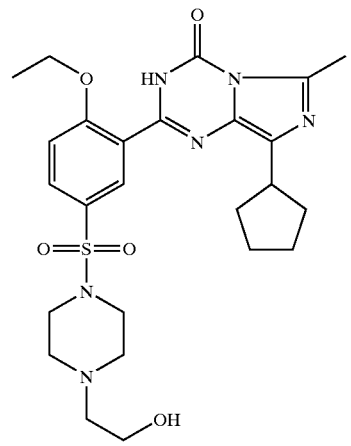

130 mg (0.3 mmol) of 4-ethoxy-3-(8-cyclopentyl-6-methyl-4-oxo-3,4-dihydro-imidazol[1,5-α][1,3,5]triazin-2-yl)-benzenesulfonyl chloride (example X) are initially introduced in 7 ml of dichloromethane. 116.2 mg (0.89 mmol) of N-hydroxyethylpiperazine are added and the mixture is subsequently stirred overnight at room temperature. Purifi cation is effected by flash chromatography using a) cyclohexane/ethyl acetate 1:1 and b) dichloromethane/methanol 95:5.

Yield: 151.4 mg (94.3% of theory)

$R_f$ value=0.477, dichloromethane/methanol 95:5

MS (DCI, $NH_3$): m/z (%)=531 (M+H) (100)

$^1$H-NMR (200 MHz, $CDCl_3$): δ=1.64 (t, 3 H); 1.67–2.08 (m, 8 H); 2.35 (bs, 1 H); 2.55–2.69 (m, 6 H); 2.87 (s, 3 H); 3.08–3.13 (m, 4 H); 3.40 (qui, 1 H); 3.59 (bt, 2 H); 4.38 (q, 2 H); 7.18 (d, 1 H); 7.83 (dd, 1 H); 8.71 (d, 1 H); 9.97 (bs, 1 H).

EXAMPLE 8

N-[2-(3,4-Dimethoxy-phenyl)-ethyl-methyl]-4-ethoxy-5-[8-cyclopentyl-6-methyl-4-oxo-3,4-dihydro-imidazo[1,5-α][1,3,5]triazin-2-yl)-benzenesulfonamide

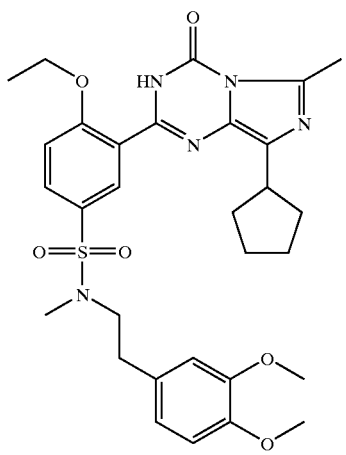

130 mg (0.3 mmol) of 4-ethoxy-3-(8-cyclopentyl-6-methyl-4-oxo-3,4-dihydro-imidazol[1,5-α][1,3,5]triazin-2-yl)-benzenesulfonyl chloride (example X) are initially introduced in 7 ml of dichloromethane. 174.3 mg (0.89 mmol) of N-methylhomoveratrylamine are added and the mixture is subsequently stirred overnight at room temperature. Purification is effected by means of flash chromatography using cyclohexane/ethyl acetate 1:1.

Yield: 144.5 g (81.5% of theory)

$R_f$ value =0.658, dichloromethane/methanol 95:5

MS (DCI, $NH_3$): m/z (%)=596 (M+H) (100)

$^1$H-NMR (200 MHz, $CDCl_3$): δ=1.65 (t, 3 H); 1.72–2.08 (m, 8 H); 2.80–2.91 (m, 8 H); 3.27–3.41 (m, 3 H); 3.88 (s, 6 H); 4.36 (q, 2 H); 6.70–6.81 (m, 3 H); 7.10 (d, 1 H); 7.81 (dd, 1 H); 8.74 (d, 1 H); 9.98 (bs, 1 H).

The sulfonamides which are listed in the following tables 1 and 2 were prepared by means of automated parallel synthesis from the sulfonyl chlorides example VI (table 1) and example X (table 2), respectively, and the corresponding amines using one of the three following standard protocols.

The purity of the end products was determined by means of HPLC while they were characterized by means of LC-MS measurement. The numerical value specified in the % (HPLC) column indicates the content of the end product which is characterized by the molar peak. Standard protocol A was used in the case of amines possessing acid functionalies, standard protocol B in the case of amines possessing neutral functionalities, and standard protocol C in the case of amines possessing additional basic functionalities.

In the case of compounds which are listed in the following tables 1 and 2 and which optically exhibit a free nitrogen valency, this latter is to be understood, in principle, as being an —NH radical.

Standard protocol A: Conversion of amines possessing acid functionalities 0.05 mmol of amine, 0.042 mmol of sulfonyl chloride and 0.10 mmol of $Na_2CO_3$ are introduced initially, and 0.5 ml of a mixture consisting of $THF/H_2O$ is pipetted in by hand. After 24 h at RT, 0.5 ml of a 1 M $H_2SO_4$ solution is added and the mixture is filtered through a two-phase cartridge (500 mg of Extrelut (upper phase) and 500 mg of $SiO_2$, mobile phase ethyl acetate). The product is obtained after concentrating the filtrate in vacuo.

Standard protocol B: Conversion of amines possessing neutral functionalities 0.125 mmol of amine is introduced initially and 0.03 mmol of sulfonyl chloride, as a solution in 1,2-dichloroethane, is pipetted in by the synthesizer. After 24 h, 0.5 ml of 1 M $H_2SO_4$ is added to the mixture and the latter is filtered through a two-phase cartridge (500 mg of Extrelut (upper phase) and 500 mg of $SiO_2$, mobile phase: ethyl acetate). The filtrate is concentrated in vacuo.

Standard protocol C: Conversion of amines possessing basic functionalities 0.05 mmol of amine is introduced initially and 0.038 mmol of sulfonyl chloride, as a solution in 1,2-dichloroethane, and 0.05 mmol of triethylamine, as a solution in 1,2-dichloroethane, are pipetted in by the synthesizer. After 24 h, 3 ml of saturated $NaHCO_3$ solution are added initially and the reaction mixture is then filtered through a two-phase cartridge. The product is obtained after the filtrate has been concentrated in vacuo.

All the reactions are monitored by thin layer chromatography. If the reaction has not been completed after 24 hours at RT, the mixture is then heated at 60° C. for a further 12 hours and the experiment is subsequently terminated.

TABLE 1

| Ex. no. | Structure | MW [g/mol] | HPLC-Area % at 210 nm | Mz + H |
|---|---|---|---|---|
| 9 | 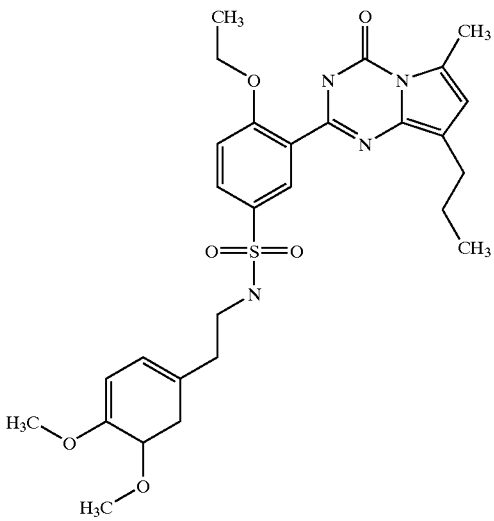 | 555.66 | 82 | 556 |
| 10 | 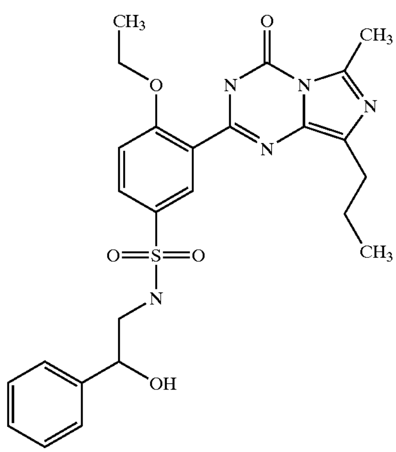 | 511.60 | 78 | 512 |
| 11 | 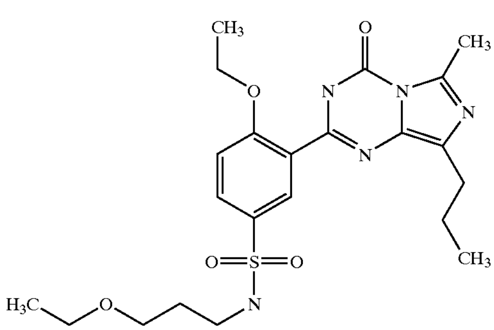 | 477.59 | 88 | 478 |

TABLE 1-continued

| Ex. no. | Structure | MW [g/mol] | HPLC-Area % at 210 nm | Mz + H |
|---|---|---|---|---|
| 12 | 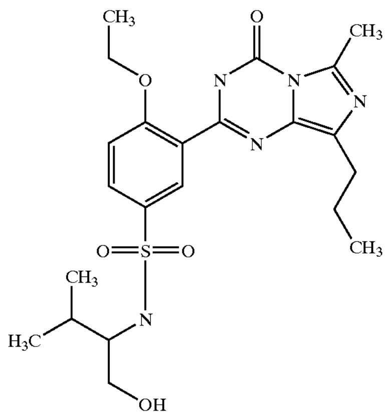 | 477.59 | 88 | 478 |
| 13 | 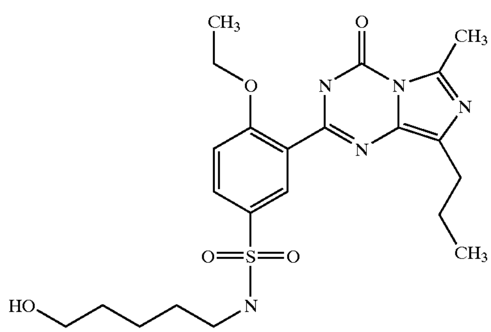 | 477.59 | 85 | 478 |
| 14 | 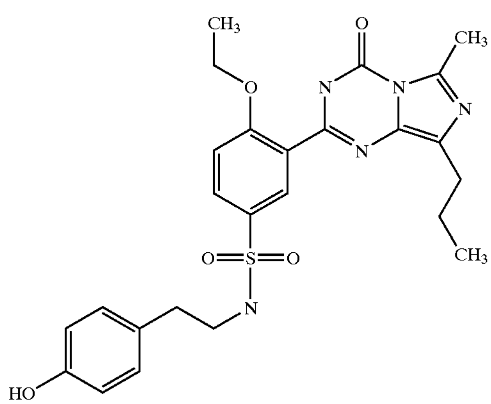 | 511.60 | 61 | 512 |
| 15 | 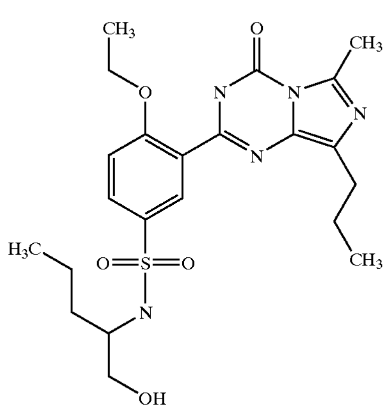 | 477.59 | 81 | 478 |

TABLE 1-continued

| Ex. no. | Structure | MW [g/mol] | HPLC-Area % at 210 nm | Mz + H |
|---|---|---|---|---|
| 16 | 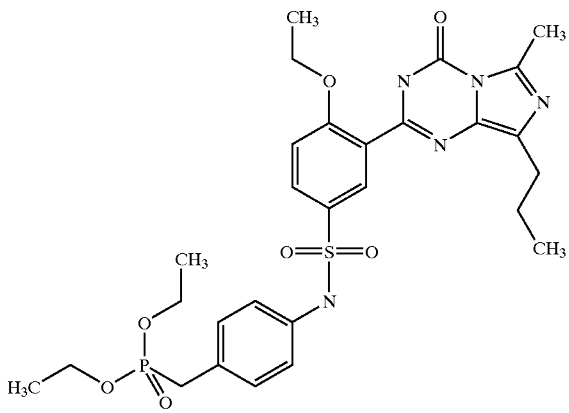 | 617.67 | 89 | 618 |
| 17 | 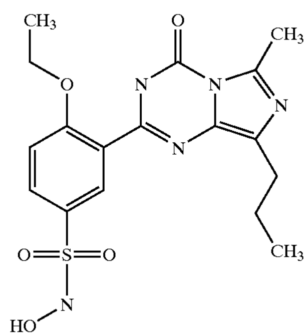 | 407.45 | 54 | 408 |
| 18 | 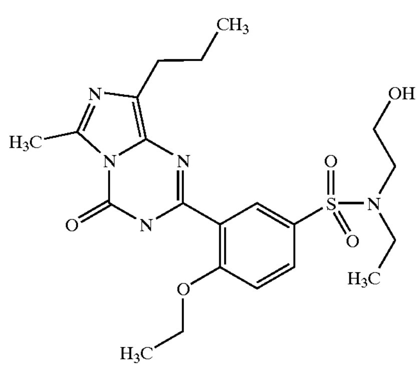 | 463.56 | 71 | 464 |
| 19 | 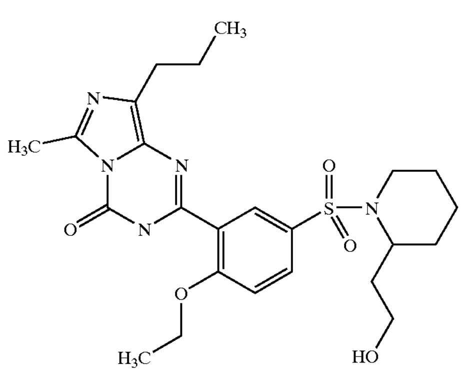 | 503.63 | 89 | 504 |

TABLE 1-continued

| Ex. no. | Structure | MW [g/mol] | HPLC-Area % at 210 nm | Mz + H |
|---|---|---|---|---|
| 20 | 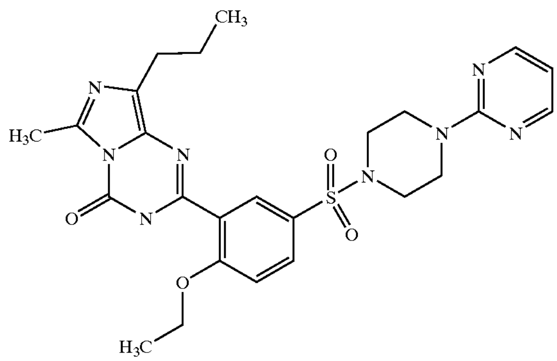 | 538.63 | 89 | 539 |
| 21 | 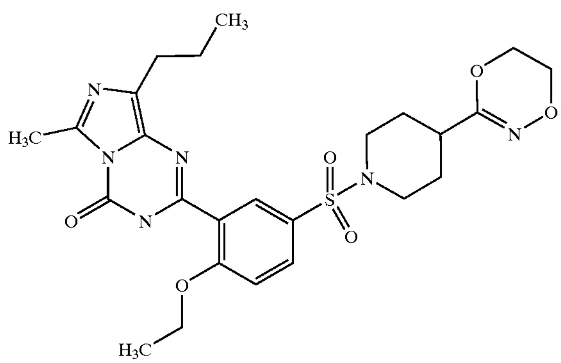 | 544.63 | 91 | 545 |
| 22 | 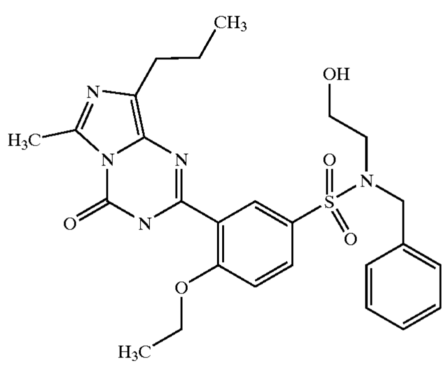 | 525.63 | 84 | 526 |
| 23 | 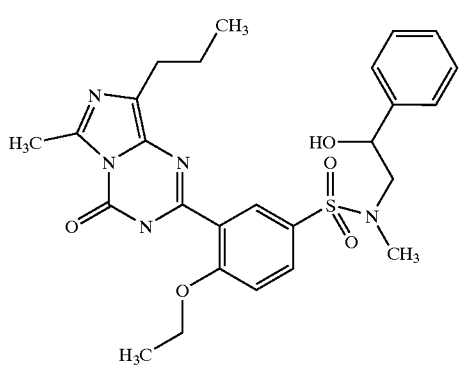 | 525.63 | 92 | 526 |

TABLE 1-continued

| Ex. no. | Structure | MW [g/mol] | HPLC-Area % at 210 nm | Mz + H |
|---|---|---|---|---|
| 24 | 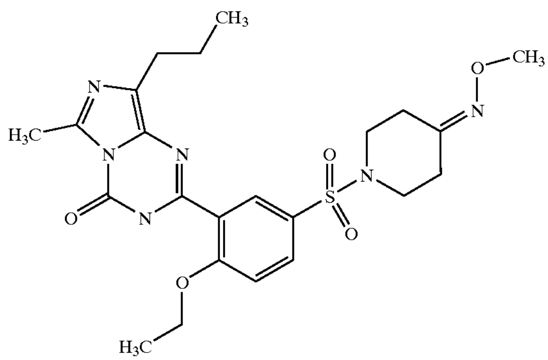 | 502.60 | 72 | 503 |
| 25 | 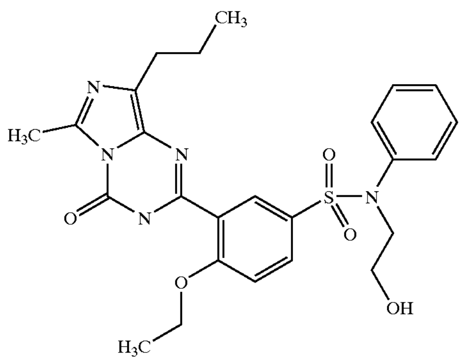 | 511.60 | 91 | 512 |
| 26 | 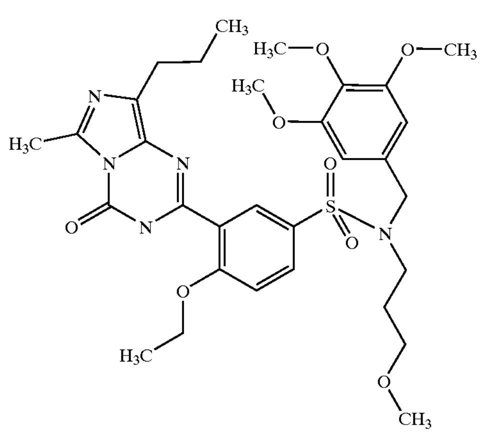 | 643.77 | 83 | 644 |
| 27 | 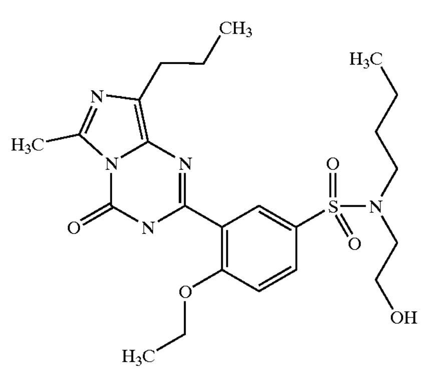 | 491.61 | 94 | 492 |

TABLE 1-continued

| Ex. no. | Structure | MW [g/mol] | HPLC-Area % at 210 nm | Mz + H |
|---|---|---|---|---|
| 28 | 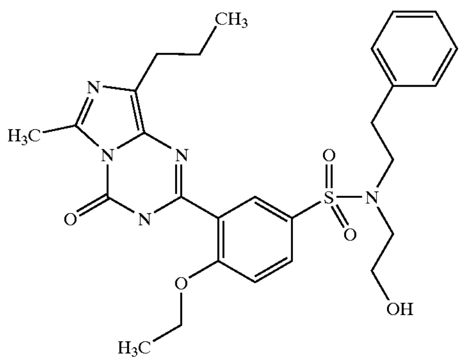 | 539.66 | 77 | 540 |
| 29 | 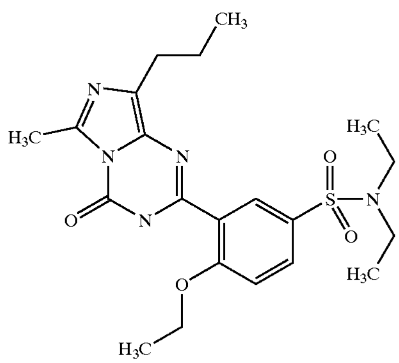 | 447.56 | 97 | 448 |
| 30 | 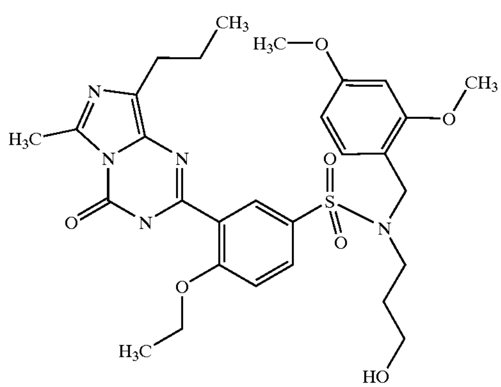 | 599.71 | 89 | 600 |
| 31 | 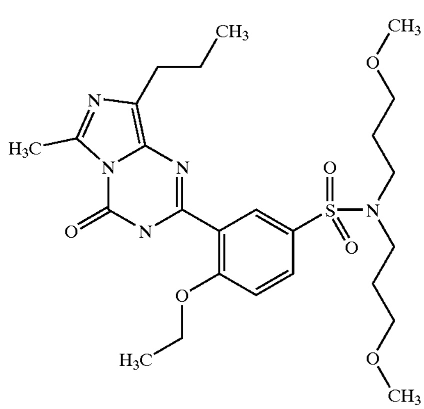 | 535.67 | 96 | 536 |

TABLE 1-continued

| Ex. no. | Structure | MW [g/mol] | HPLC-Area % at 210 nm | Mz + H |
|---|---|---|---|---|
| 32 | 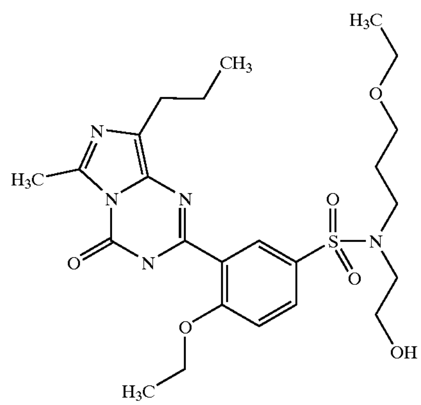 | 521.64 | 75 | 522 |

TABLE 2

| Ex. no. | Structure | MW [g/mol] | HPLC % (210 nm) | Mz + H |
|---|---|---|---|---|
| 33 | 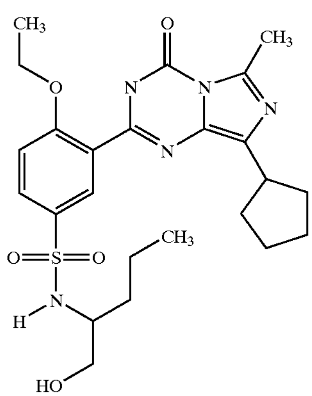 | 503.63 | 76 | 504 |
| 34 | 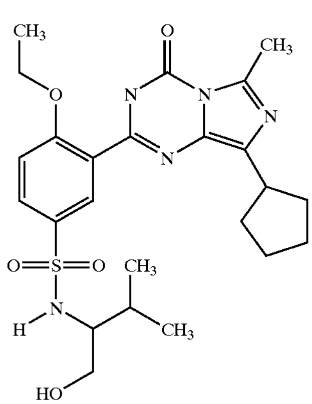 | 503.63 | 86 | 504 |
| 35 | | 503.63 | 75 | 504 |
| 36 | | 489.60 | 80 | 490 |

TABLE 2-continued
| Ex. no. | Structure | MW [g/mol] | HPLC % (210 nm) | Mz + H |
|---|---|---|---|---|
| 37 | 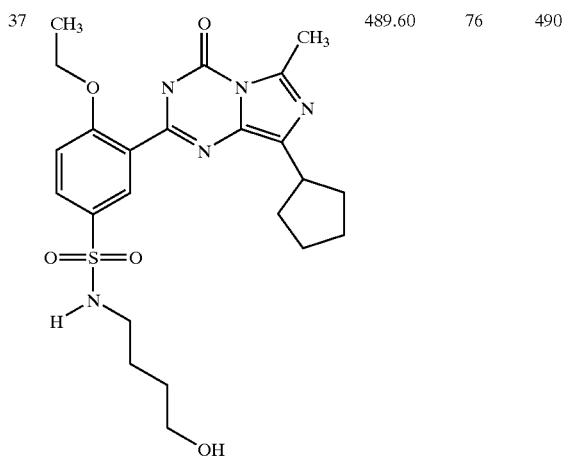 | 489.60 | 76 | 490 |
| 38 | 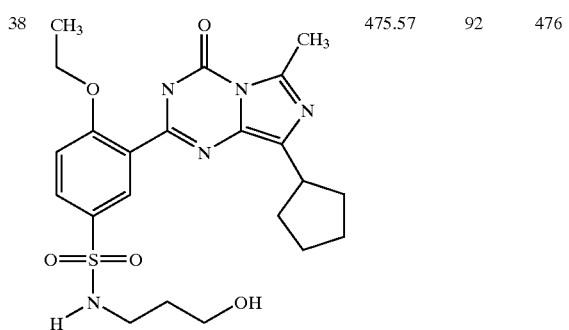 | 475.57 | 92 | 476 |
| 39 | 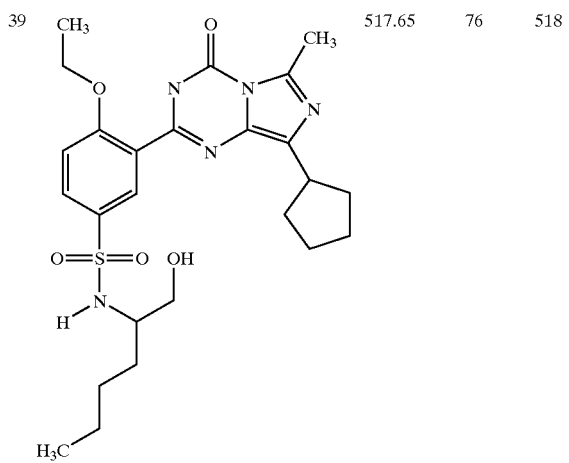 | 517.65 | 76 | 518 |
| 40 | 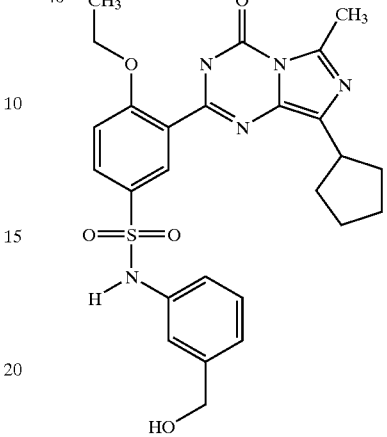 | 523.62 | 79 | 524 |
| 41 | 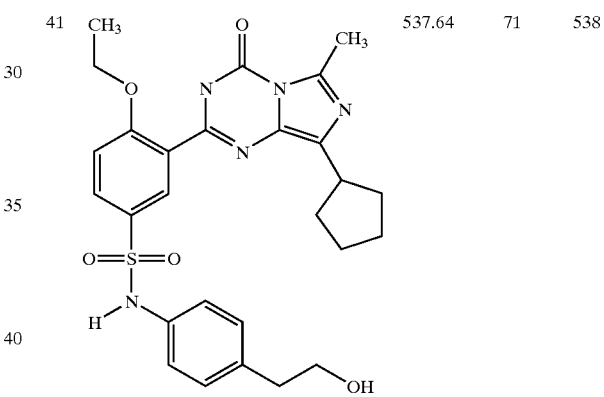 | 537.64 | 71 | 538 |
| 42 | 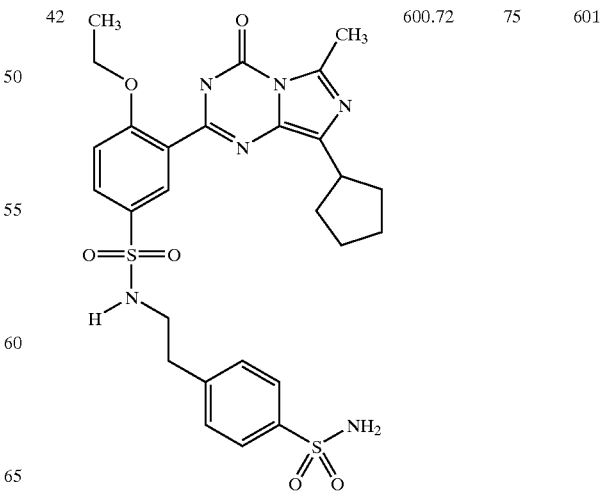 | 600.72 | 75 | 601 |

TABLE 2-continued

| Ex. no. | Structure | MW [g/mol] | HPLC % (210 nm) | Mz + H |
|---|---|---|---|---|
| 43 | 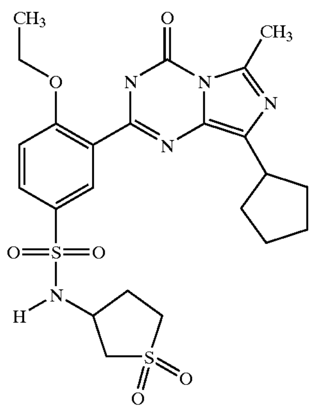 | 535.65 | 72 | 536 |
| 44 | 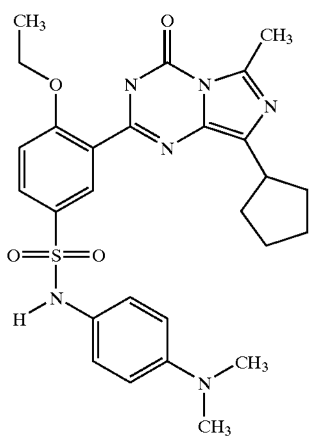 | 536.66 | 65 | 537 |
| 45 | 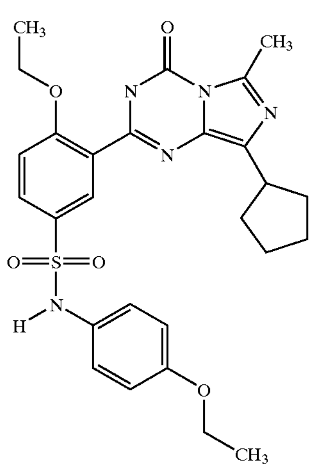 | 537.64 | 83 | 538 |
| 46 | | 607.73 | 69 | 608 |
| 47 | | 523.62 | 84 | 524 |
| 48 | | 553.64 | 82 | 554 |

TABLE 2-continued

| Ex. no. | Structure | MW [g/mol] | HPLC % (210 nm) | Mz + H |
|---|---|---|---|---|
| 49 | 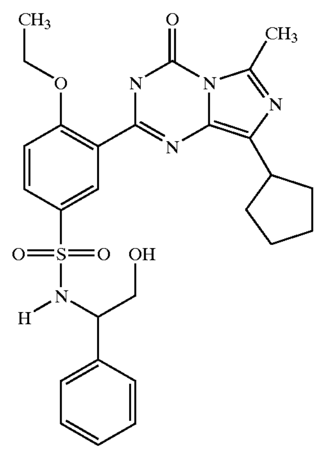 | 537.64 | 74 | 538 |
| 50 | 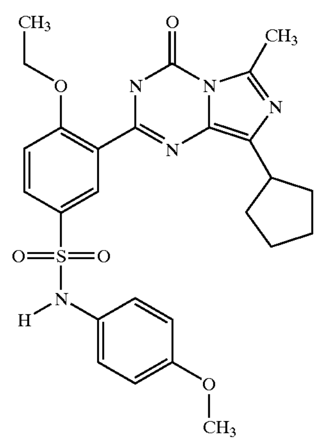 | 523.62 | 88 | 524 |
| 51 | 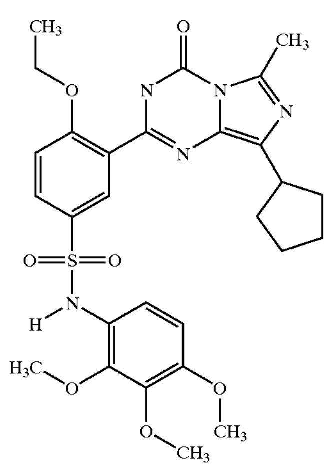 | 583.67 | 89 | 584 |
| 52 | | 544.68 | 78 | 545 |
| 53 | | 537.64 | 78 | 538 |
| 54 | | 475.57 | 83 | 476 |

TABLE 2-continued
| Ex. no. | Structure | MW [g/mol] | HPLC % (210 nm) | Mz + H |
|---|---|---|---|---|
| 55 | 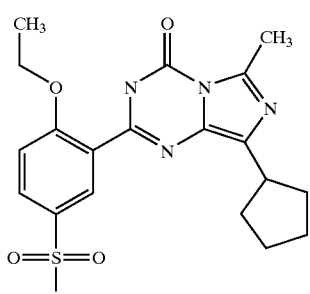 | 447.52 | 86 | 448 |
| 56 | 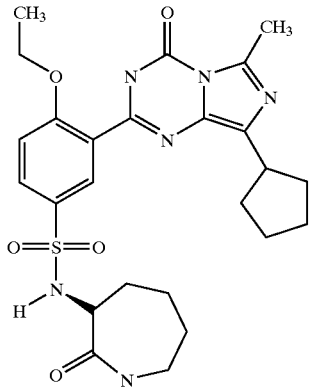 | 528.63 | 70 | 529 |
| 57 | 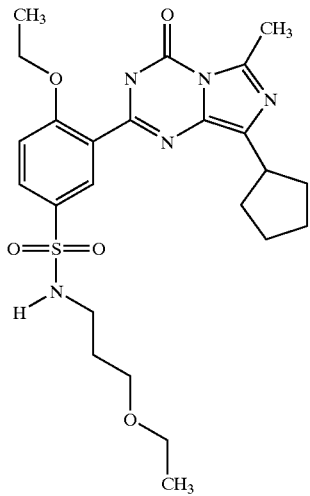 | 503.63 | 91 | 504 |
| 58 | 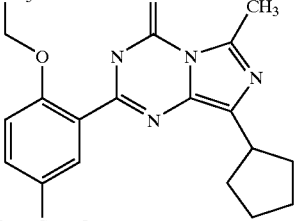 | 503.63 | 75 | 504 |
| 59 | 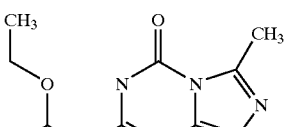 | 550.68 | 88 | 551 |
| 60 | 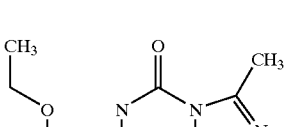 | 537.64 | 78 | 538 |

TABLE 2-continued

| Ex. no. | Structure | MW [g/mol] | HPLC % (210 nm) | Mz + H |
|---|---|---|---|---|
| 61 | 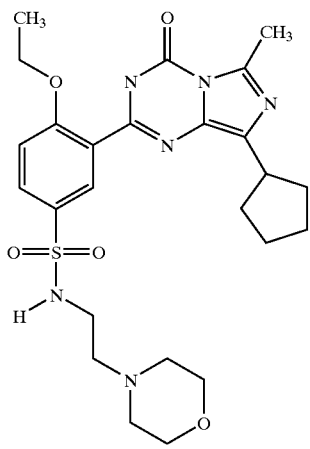 | 530.65 | 75 | 531 |
| 62 | 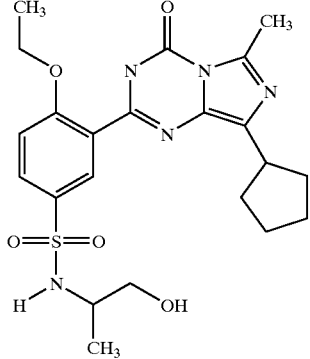 | 475.57 | 81 | 476 |
| 63 | 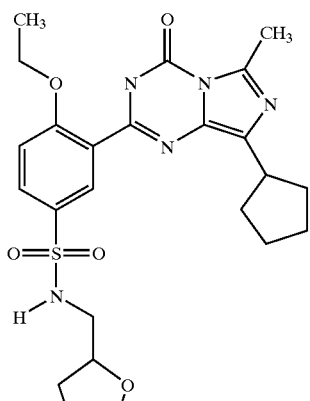 | 501.61 | 94 | 502 |

What is claimed is:

1. An imidazo[1,3,5]triazinone of formula (I)

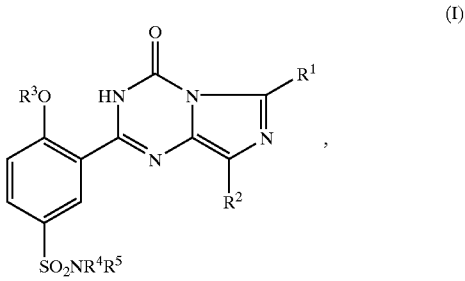

in which

R$^1$ represents straight-chain or branched alkyl having up to 4 carbon atoms,

R$^2$ represents straight-chain or branched alkyl having up to 4 carbon atoms or represents (C$_3$–C$_8$)-cycloalkyl, R$^3$ represents hydrogen or straight-chain or branched alkyl having up to 4 carbon atoms, R$^4$ and R$^5$ are identical or different and represent hydrogen, (C$_1$–C$_6$)-alkoxy or hydroxyl or represent (C$_1$–C$_8$)-alkyl which is optionally substituted, up to 3 times, identically or differently, by hydroxyl or (C$_1$–C$_6$)-alkoxy or by radicals of the formulae

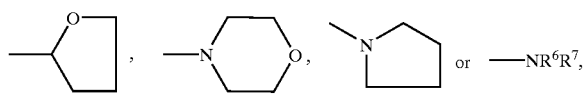

in which

R$^6$ and R$^7$ are identical or different and denote hydrogen or (C$_1$–C$_6$)-alkyl, and/or, for its part, (C$_1$–C$_8$)-alkyl is optionally substituted by phenyl or phenoxy which, for their part, are optionally substituted, once to three times, identically or differently, by halogen, hydroxyl, (C$_1$–C$_6$)-alkoxy or (C$_1$–C$_6$)-alkyl or by a radical of the formula —SO$_2$NR$^8$R$^9$, in which R$^8$ and R$^9$ are identical or different and denote hydrogen or (C$_1$–C$_6$)-alkyl, or R$^4$ represents hydrogen or methyl, and R$^5$ represents radicals of the formulae

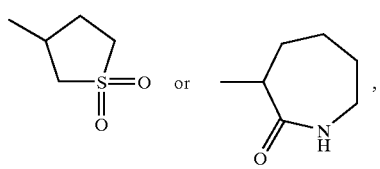

or represents phenyl which is optionally substituted, up to 3 times, identically or differently, by halogen, acetyl or (C$_1$–C$_6$)-alkoxy or by radicals of the formulae

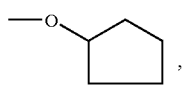

—NR$^{10}$R$^{11}$ or —CH$_2$—P(O)(OR$^{12}$)(OR$^{13}$)

in which

R$^{10}$ and R$^{11}$ are identical or different and denote hydrogen or (C$_1$–C$_4$)-alkyl, R$^{12}$ and R$^{13}$ are identical or different and denote hydrogen or (C$_1$–C$_6$)-alkyl, or R$^4$ and R$^5$, together with the nitrogen atom to which they are bonded, form radicals of the formulae

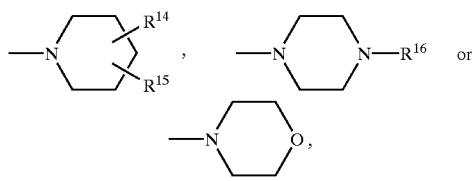

in which

R$^{14}$ and R$^{15}$ are identical or different and denote hydroxyl, hydrogen or (C$_1$–C$_4$)-alkyl which is optionally substituted by hydroxyl, or R$^{14}$ denotes hydrogen, and R$^{15}$ denotes a radical of the formula

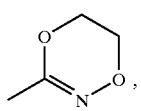

or

R$^{14}$ and R$^{15}$ together form a radical of the formula =N—O—CH$_3$,

R$^{16}$ denotes hydrogen or (C$_1$–C$_6$)-alkyl which is optionally substituted by hydroxyl, or a 5- to 6-membered, aromatic heterocycle having up to 3 heteroatoms from the series S, N and/or O, or the salts, N-oxides and isomeric forms thereof.

2. An imidazo[1,3,5]triazinone of formula (I) as claimed in claim 1, in which

R$^1$ represents methyl or ethyl,

R$^2$ represents straight-chain or branched alkyl having up to 3 carbon atoms or represents (C$_3$–C$_6$)-cycloalkyl, R$^3$ represents straight-chain or branched alkyl having up to 3 carbon atoms, R$^4$ and R$^5$ are identical or different and represent hydrogen, (C$_1$–C$_4$)-alkoxy or hydroxyl or represent (C$_1$–C$_7$)-alkyl which is optionally substituted, up to 3 times, identically or differently, by hydroxyl or (C$_1$–C$_4$)-alkoxy or by radicals of the formulae

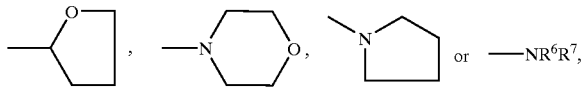

in which

R$^6$ and R$^7$ are identical or different and denote hydrogen or methyl, and/or, for its part, (C$_1$–C$_7$)-alkyl is optionally substituted by phenyl or phenoxy which, for their part, are optionally substituted, once to three times, identically or differently, by fluorine, chlorine, hydroxyl, (C$_1$–C$_4$)-alkoxy or (C$_1$–C$_4$)-alkyl or by a radical of the formula —SO$_2$NH$_2$, or R$^4$ represents hydrogen or methyl, and R$^5$ represents radicals of the formulae

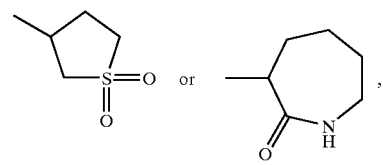

or represents phenyl which is optionally substituted, up to 3 times, identically or differently, by fluorine, chlorine, acetyl or (C$_1$–C$_4$)-alkoxy or by radicals of the formulae

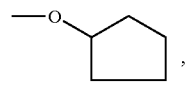

—NR$^{10}$R$^{11}$ or —CH$_2$—P(O)(OR$^{12}$)(OR$^{13}$)

in which

R$^{10}$ and R$^{11}$ are identical or different and denote hydrogen or methyl,

R$^{12}$ and R$^{13}$ are identical or different and denote hydrogen or methyl, or R$^4$ and R$^5$, together with the nitrogen atom to which they are bonded, form radicals of the formulae

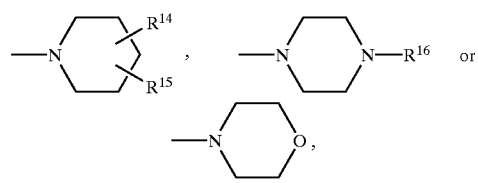

in which

R$^{14}$ and R$^{15}$ are identical or different and denote hydroxyl, hydrogen or (C$_1$–C$_3$)-alkyl which is optionally substituted by hydroxyl, or R$^{14}$ denotes hydrogen, and R$^{15}$ denotes a radical of the formula

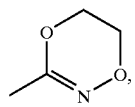

or $R^{14}$ and $R^{15}$ together form a radical of the formula =N—O—CH$_3$, $R^{16}$ denotes hydrogen or (C$_1$–C$_5$)-alkyl which is optionally substituted by hydroxyl, or denotes pyridyl, pyrimidyl, furyl, pyrryl or thienyl, or the salts, N-oxides and isomeric forms thereof.

3. An imidazo[1,3,5]triazinone of formula (I) as claimed in claim 1, in which $R^1$ represents methyl or ethyl, $R^2$ represents n-propyl or represents cyclopentyl, $R^3$ represents methyl, ethyl or n-propyl, $R^4$ and $R^5$ are identical or different and represent hydrogen, (C$_1$–C$_3$)-alkoxy or hydroxyl or represent (C$_1$–C$_6$)-alkyl which is optionally substituted, up to 3 times, identically or differently, by hydroxyl or (C$_1$–C$_3$)-alkoxy or by radicals of the formulae

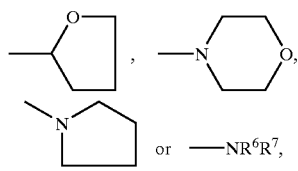

or —NR$^6$R$^7$, in which $R^6$ and $R^7$ are identical or different and denote hydrogen or methyl, and/or, for its part, (C$_1$–C$_6$)-alkyl is optionally substituted by phenyl or phenoxy which, for their part, are optionally substituted, once to three times, identically or differently, by fluorine, hydroxyl or methoxy or by a radical of the formula —SO$_2$NH$_2$, or $R^4$ represents hydrogen or methyl, and $R^5$ represents radicals of the formulae

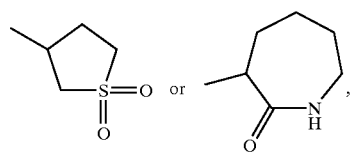

or represents phenyl which is optionally substituted, up to 3 times, identically or differently, by fluorine, acetyl or methoxy or by radicals of the formulae

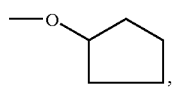

—NR$^{10}$R$^{11}$ or —CH$_2$—P(O)(OR$^{12}$)(OR$^{13}$)

in which $R^{10}$ and $R^{11}$ are identical or different and denote hydrogen or methyl, $R^{12}$ and $R^{13}$ denote methyl, or $R^4$ and $R^5$, together with the nitrogen atom to which they are bonded, form radicals of the formulae

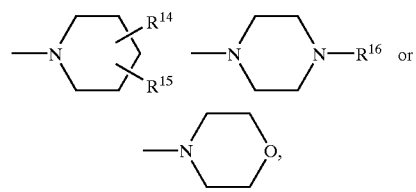

in which $R^{14}$ and $R^{15}$ are identical or different and denote hydroxyl, hydrogen or a radical of the formula —(CH$_2$)$_2$—OH, or $R^{14}$ denotes hydrogen, and $R^{15}$ denotes a radical of the formula

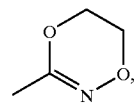

or $R^{14}$ and $R^{15}$ together form a radical of the formula =N—O—CH$_3$, $R^{16}$ denotes hydrogen, pyrimidyl or a radical of the formula —(CH$_2$)$_2$—OH, or the salts, N-oxides and isomeric forms thereof.

4. An imidazo[1,3,5]triazinone of formula (I) as claimed in any one of claims 1 to 3 and having one of the following structures:

| Structure |
| --- |
| 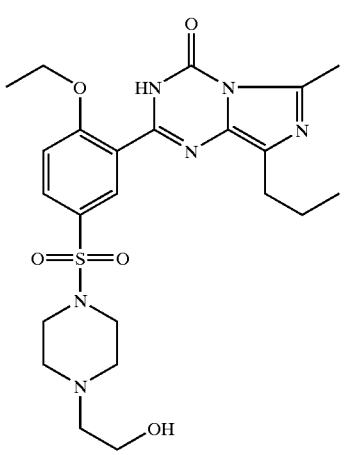 |

| Structure |
|---|
| 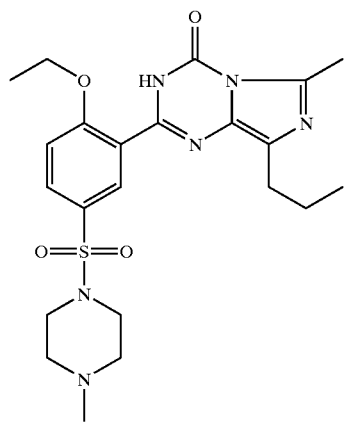 |
| 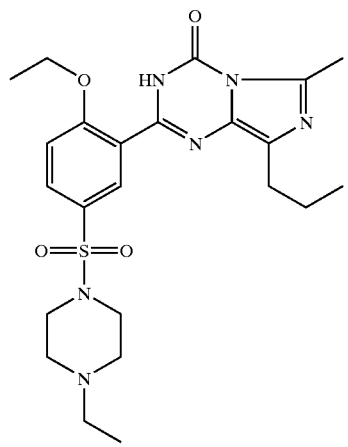 |
| 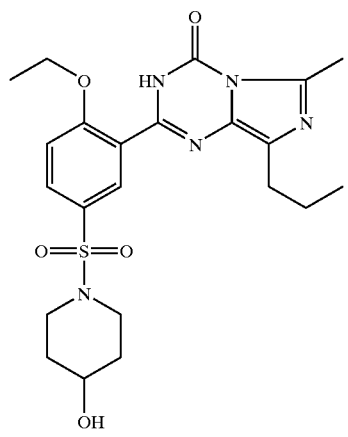 |
| Structure |
|---|
| 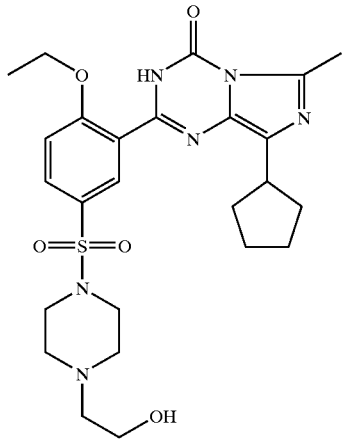 |
| 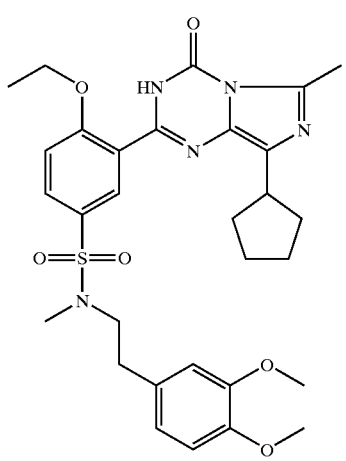 |
5. A process for preparing imidazo[1,3,5]triazinones as claimed in claims 1, characterized in that compounds of the general formula (II)
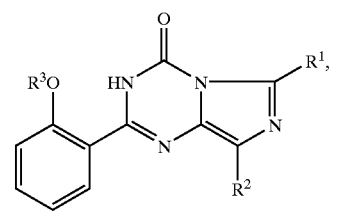

in which $R^1$, $R^2$ and $R^3$ have the abovementioned meaning in claim 1, are first of all converted, by reaction with chlorosulfonic acid (ClSO$_3$H) into the compounds of the general formula (III)

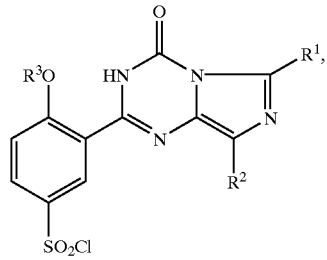 (III)

in which $R^1$, $R^2$ and $R^3$ have the abovementioned meaning in claim 1, and, in a last step, are reacted with amines of the general formula (IV)

$$HN—R^4R^5 \qquad (IV),$$

in which $R^4$ and $R^5$ have the abovementioned meaning in claim 1.

6. A pharmaceutical composition comprising one or more compounds of claim 1 and one or more inert carriers.

7. A method of treating diseases of the urogenital system, comprising administering to a mammal an effective amount of a compound of claim 1.

8. The method of claim 7, wherein said urogenital system disease is selected from prostate hypertrophy, incontinence, erectile dysfunction and female sexual dysfunction.

9. The method of claim 7, wherein said compound of claim 1 is administered intravenously or orally.

* * * * *